(12) United States Patent
Naito et al.

(10) Patent No.: US 8,309,576 B2
(45) Date of Patent: Nov. 13, 2012

(54) METHOD OF TREATING INFLAMMATORY BOWEL DISEASE

(75) Inventors: Yuji Naito, Kyoto (JP); Naoto Koyama, Kawasaki (JP); Katsuya Suzuki, Kawasaki (JP); Hideaki Kihara, Kawasaki (JP); Yuka Ikenoue, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 12/267,907

(22) Filed: Nov. 10, 2008

(65) Prior Publication Data

US 2009/0156657 A1 Jun. 18, 2009

Related U.S. Application Data

(63) Continuation of application No. PCT/JP2007/059621, filed on May 9, 2007.

(30) Foreign Application Priority Data

May 10, 2006 (JP) ................................. 2006-131770

(51) Int. Cl.
*A61K 31/445* (2006.01)
*A61K 36/00* (2006.01)
(52) U.S. Cl. .......................... 514/315; 424/783; 424/776
(58) Field of Classification Search ........................ None
See application file for complete search history.

(56) References Cited

U.S. PATENT DOCUMENTS

| 2005/0136137 | A1 | 6/2005 | Koyama et al. |
| 2006/0257540 | A1 | 11/2006 | Koyama et al. |
| 2007/0009618 | A1 | 1/2007 | Koyama et al. |
| 2008/0171781 | A1 | 7/2008 | Katsuda et al. |

FOREIGN PATENT DOCUMENTS

| WO | WO 03/086437 A1 | 10/2003 |
| WO | WO 2005/034975 A1 | 4/2005 |
| WO | WO 2007/032551 A1 | 3/2007 |

OTHER PUBLICATIONS

Kang, Kiyoon, et al, "Enhanced Neutraceutical Serotonin Derivatives of Rice Seed by Hydroxycinnamoyl-CoA: Serotonin N-(hydroxycinnamoyl) Transferase," Plant Science, vol. 168, pp. 783-788 (2005).*
Sachiko Kawashima, et al., "Serotonin Derivative, N-(p-Coumaroyl) Serotonin, Inhibits the Production of TNF-α, IL-1α, IL-1β, and IL-6 by Endotoxin-Stimulated Human Blood Monocytes", Journal of Interferon and Cytokine Research, vol. 18, No. 6, 1998, pp. 423-428.
New Release (Jul. 11, 2007) [online] URL: http://www.ajinomoto.cojp/press/2007-07.html , 12 pages with English translation.
Barry Halliwell, "Free Radicals in Biology and Medicine", Third Edition, Oxford Science Publications, 1999, pp. 324-327.
Susana Martinez-Florez, et al., "Quercetin Attenuates Nuclear Factor-kB Activation and Nitric Oxide Production in Interleukin-1β-Activated Rat Hepatocytes", The Journal of Nutrition, vol. 135, Mar. 9, 2005, pp. 1359-1365.
Chi-Hsiao Yeh, MD, et al., "Inhibition of NF kB Activation with Curcumin Attenuates Plasma Inflammatory Cytokines Surge and Cardiomyocytic Apoptosis Following Cardiac Ischemia/ Reperfusionl[1]", Journal of Surgical Research, vol. 125, No. 1, May 2005, pp. 109-116.
Chun-Mao Lin, et al., "Isovitexin Suppresses Lipopolysaccharide-Mediated Inducible Nitric Oxide Synthase through Inhibition of NF-kappa B in Mouse Macrophages", Planta Medica, vol. 71, Aug. 11, 2005, pp. 748-753.
Mary E. Gerritsen, et al., "Flavonoids Inhibit Cytokine-Induced Endothelial Cell Adhesion Protein Gene Expression", American Journal Pathology, vol. 147, No. 2, Aug. 1995, pp. 278-292.
Yoshimasa Nakamura, et al., "Inhibitory Effects of Curcumin and Tetrahydrocurcuminoids on the Tumor Promoter-induced Reactive Oxigen Species Generation in Leukocytes in vitro and in vivo", Jpn.J. Cancer Res., vol. 89, Apr. 1998, pp. 361-370.
Chiemi Kamada, et al., "Attenuation of lipid peroxidation and hyperlipidemia by quercetin glucoside in aorta of high cholesterol-fed rabbit", Free Radical Research, vol. 39, No. 2, Feb. 2005, pp. 185-194.
G. Williamson, et al., "In vitro biological properties of flavonoid conjugates found in vivo", Free Radical Research, vol. 39, No. 5, May 2005, pp. 457-469.
Takemasa Takii, et al., "Multiple mechanisms involved in the inhibition of proinflammatory cytokine production from human monocytes by N-(p-coumaroyl) serotonin and its derivatives", International Immunopharmacology, vol. 3, 2003, pp. 273-277.
M.A. Grusak, "Phytochemicals in plants: genomics-assisted plant improvement for nutritional and health benefits", Curr. Opin. Biotechnol., 2002, pp. 508-511.
Y. Hotta et al, "Protective effects of antioxidative serotonin derivatives isolated from safflower against postischemic myocardial dysfunction", Molecular and Cellular Biochemistry, 2002, 238, pp. 151-162.
A. Nagatsu et al, "Tyrosinase Inhibitory and Anti-Tumor Promoting Activities of Compounds Isolated from Safflower (Carthamus tinctorius L.) and Cotton (Gossypium hirsutum L.) Oil Cakes", Natural Product Letters, 2000, vol. 14(3), pp. 153-158.
S.H. Cho et al, "Effects of Defatted Safflower Seed Extract and Phenolic Compounds in Diet on Plasma and Liver Lipid in Ovariectomized Rats Fed High-Cholesterol Diets", J. Nutr. Sci. Vitaminol., 2004, 50, pp. 32-37.
Japanese Office Action dated Aug. 7, 2012 in corresponding Japanese Patent Application No. 2008-514517 with English Translation (13 pp.).

* cited by examiner

*Primary Examiner* — Nancy T Vogel
*Assistant Examiner* — Catherine Hibbert
(74) *Attorney, Agent, or Firm* — Oblon, Spivak, McClelland, Maier & Neustadt, L.L.P.

(57) ABSTRACT

The present invention provides a method of improving or treating inflammatory bowel disease through suppression of the expression of inflammatory cytokines based on the action mechanism of suppression of NF-κB activation by administering feruloyl serotonin to a subject in need of treatment of inflammatory bowel disease. The feruloyl serotonin of the present invention can be administered as a pharmaceutical agent or a food.

11 Claims, 11 Drawing Sheets p<0.01, ### p<0.001 vs normal (t-test)
* p<0.05,  p<0.01, * p<0.001 vs control
(Dunnett test)

### p<0.001 vs normal (t-test)

* p<0.05,  p<0.01, * p<0.001 vs control (Dunnett test)

## p<0.01 vs Normal (t-test)
** p<0.01 vs Control (Tukey test)

METHOD OF TREATING INFLAMMATORY BOWEL DISEASE

CROSS REFERENCES TO RELATED APPLICATIONS

This application is a continuation of International Patent Application No. PCT/JP2007/059621, filed on May 9, 2007, and claims priority to Japanese Patent Application No. 2006-131770, filed on May 10, 2006, both of which are incorporated herein by reference in their entireties.

BACKGROUND OF THE INVENTION

1. Field of the Invention

The present invention relates to methods and agents useful for suppressing NF-κB activation. The present invention also relates to methods and agents useful for treating and/or preventing inflammation. The present invention further relates to methods and agents useful for the treatment or prophylaxis of diseases caused by NF-κB activation.

2. Discussion of the Background

Inflammation is a biological response to various exogenous or endogenous tissue-damaging stimuli. When a part of the body tissue is damaged by infection and the like, various biological response-modifying substances are produced in and released from the tissue, and cause inflammation. In the initial stages, inflammatory cytokines such as TNF-α, IL-1 and the like are produced in the inflammation site, expression of cell adhesion factors (ICAM-1, VCAM-1 etc.) on the vascular endothelium is enhanced by the action of the cytokines, and adhesion of the inflammatory cells to the vascular wall is promoted. Simultaneously, monocytes, lymphocytes and neutrophils infiltrate into the inflammation tissue due to the chemotactic factors produced in the inflammation site, such as MCP-1, IL-8 and the like. While various cytokines, active oxygen, hydrolase and the like are additionally secreted from the subendothelially infiltrated inflammatory cells against pathogenic microorganisms and the like, they also damage the host tissue at the same time. When the proinflammatory substance is eradicated or removed through such processes, infiltration of the inflammatory cell generally stops and the inflammation progresses towards dissipation. When the tissue damage is high, however, it is not repaired completely, and the parenchymal cell is replaced (fibrosed) by connective tissues, sometimes causing dysfunction of the tissue. In addition, continuous infection such as tuberculosis, self-tissue damage due to autoimmune mechanism, accumulation of oxidized LDL and the like prolong inflammation and sometimes form pathology of repeated active inflammatory response, tissue destruction and tissue repair over a long period, which is called chronic inflammation. Quite a number of such chronic inflammatory diseases are intractable, such as Behcet's disease and the like, and patients suffer from decreased quality of life (QOL) for a long time.

In these inflammation processes, many genes are activated, and NF-κB is a transcription factor playing a key role in the gene activation process. It is known that NF-κB is a heterodimer consisting of two subunits p50 and p65, and usually present in the cytoplasm in an inert form of a complex with I-κB, which is an inhibitory protein. It is known that, when stimulated, however, I-κB is degraded by phosphorylation and released from the complex, then the NF-κB heterodimer is translocated into the nucleus, binds to DNA and regulates the gene expression in the downstream of the binding site. It is said that oxidative stress is involved in the process of activation of NF-κB and translocation into the nucleus. While the mechanism thereof is yet to be clarified in a number of aspects, it is considered that a certain kind of reactive oxygen species (ROS) activates I-κB kinase and promotes degradation of I-κB. Addition of a plurality of antioxidants and over-expression of antioxidant enzymes such as glutathione peroxidase and the like are known to suppress activation of NF-κB. Conversely, binding of activated NF-κB, which is translocated into the nucleus, onto a DNA is inhibited by an oxidant and promoted by thiols. Thus, it can be said that activation of NF-κB and subsequent expression of various gene products are both under the control of redox. However, since the manner of control is different, the influence of the changes in the intracellular redox state on the gene product expression under the control of NF-κB is not always uniform but complicated (see, Halliwell B and Gutteridge J M, Free Radicals in Biology and Medicine Third Edition, Oxford Science Publications (1999)). Representative examples of the gene products subject to expression control by NF-κB include inflammatory cytokines such as TNF-α, IL-1β, IL-6 and the like; cell adhesion factors such as ICAM-1, VCAM-1, E-selectin and the like; cell chemotactic factors (chemokine) such as IL-8 or MCP-1 and the like; inducible nitric oxide synthase (iNOS); tissue factor (TF); inducible cyclooxygenase (COX-2); and the like. Activation of NF-κB is considered to be involved in many diseases. Examples of important diseases include atherosclerosis, myocardial infarction, virus infection (HIV, cytomegalovirus and the like), arthritis (chronic rheumatoid arthritis, osteoarthritis and the like), psoriasis, inflammatory bowel disease (IBD), type II diabetes, bronchial asthma, sepsis, autoimmune diseases and the like.

VCAM-1 (Vascular Cell Adhesion Molecule-1), which shows increased expression by the activation of NF-κB, is a glycoprotein having a molecular weight of 110 kDa, and the expression thereof is mainly observed in vascular endothelial cells, macrophages and the like. The main action thereof is to strongly adhere leukocytes onto vascular endothelial cells by binding to VLA4, one of the members of the β1-integrin family, which is expressed in lymphocytes, monocytes and the like. As for the relationship between VCAM-1 and diseases, increased expression of VCAM-1 has been confirmed in the vascular endothelial cells of topical lesions of various acute/chronic inflammatory diseases such as atherosclerosis, allograft rejection, metastasis of malignant tumor (melanoma etc.) and the like.

MCP-1 (Monocyte Chemotactic Protein-1) is produced by endothelial cells, smooth muscle cells, macrophages and the like, and strongly induces subendothelial migration of monocyte/macrophage and T lymphocyte adhered to the vascular endothelial cell. Therefore, MCP-1 is considered to promote tissue infiltration of monocyte and T cell at various inflammatory lesions. MCP-1 is also known to have associations with many diseases, and is reported to show enhanced production at topical sites, as well as improvement of symptoms by MCP-1 neutralization antibody/antagonist and the like, in chronic inflammatory diseases such as bronchial asthma, allergic rhinitis, chronic rheumatoid arthritis, lung hypertension, hepatic fibrosis, renal sclerosis, viral encephalitis, atherosclerosis, endometriosis, inflammatory bowel disease (IBD) and the like, and allergic disease/immune abnormality.

While various anti-inflammatory agents are used for treating inflammatory diseases, a decisive agent which suppresses production of various inflammatory mediators or expression of inflammatory cell adhesion molecules has not been found. One of the reasons therefor is that blocking of a single enzyme activity or single cytokine production is considered to be insufficient, since many gene products are involved in inflammatory responses, as mentioned above. For example, NSAIDs (non-steroidal anti-inflammatory drugs) suppress production of inflammatory prostaglandin by inhibiting cyclooxygenase in arachidonic acid metabolism, but they do not directly inhibit cytokine production. Even if an anticytokine therapy using a cytokine antibody or a cytokine receptor blocker and the like can suppress function of a particular cytokine, it cannot directly suppress the activity of plural cytokines. For example, anti-ICAM-1 antibody is reported to be effective for suppressing rejection during organ transplantation and the like, but it does not have a direct action on other adhesion molecules or inflammatory cytokines. In addition, although anti-cytokine therapy shows a high initial administration effect, the duration of the effect is questioned, and clinical application thereof to chronic inflammatory diseases is considered to be difficult. Meanwhile, conventional anti-inflammatory agents containing an immunosuppressant and anti-cytokine therapy reportedly cause many side effects. For example, steroids can be administered orally and advantageously non-specifically suppress production of plural cytokines. On the other hand, it includes the problems of aggravated infection, rebound and the like. Although anti-TNF-α antibody shows an effect on chronic rheumatoid arthritis and Crohn's disease, serious problems of infectious diseases, allergy (anaphylactic shock) and the like have been pointed out.

Since NF-κB suppressive agents inhibit a common process in the activation of a gene involved in the production of the aforementioned various inflammation causative substances, in contrast to the existing anti-inflammatory agents, there is a possibility that such agents may act widely and anti-inflammatorily. In other words, since the agent simultaneously suppresses transcription of a plurality of inflammatory cytokines, it may be applied to a pharmaceutical product for treating diseases caused by abnormal production of inflammatory cytokines, an antiviral agent against viruses requiring activation of NF-κB for self-replication, such as HIV, cytomegalovirus and the like, an anti-inflammatory agent or cancer metastasis suppressant based on the suppression of expression of cell adhesion molecules, an immunosuppressant used in organ transplantation, and the like.

Some natural components contained in food and the like are also known to have an NF-κB suppressive action (quercetin (see, Martinez-Florez S et al., J. Nutr. 135:1359-1365 (2005)), curcumin (see, Yeh C-H et al., J. Surgical Res. 125: 109-116 (2005)), isovitexin (see, Lin C-M et al., Planta Medica 71:748-753 (2005)), apigenin (see, Gerritsen M E et al., Am. J. Pathol. 147:278-292 (1995)), pycnogenol (see, Packer L, Book of abstracts, 219th ACS National Meeting, San Francisco, Calif., Mar. 26-30, (2000)), and the like). These polyphenols are taken orally, considered to have comparatively high safety, and some of them are reported to show an antioxidant activity and an anti-atherosclerosis action and the like (see, Nakamura Y et al., Jpn. J. Cancer Res. 89:361-370 (1998) and Karnada C et al., Free Rad. Res. 39:185-194 (2005)). Therefore, they may be useful for daily control of chronic inflammatory condition or prevention of the onset of inflammatory diseases. However, these suppressive actions of NF-κB were examined in vitro, whereas polyphenols are reportedly metabolized in the body to show an attenuated antioxidant action or lose the action (see, Williamson G et al., Free Rad Res. 39:457-469 (2005)). Therefore, it is unknown whether these substances actually show an anti-inflammatory action in the body.

Safflower seed defatted meal extracts are shown to strongly suppress oxidation of low-density lipoprotein (LDL) in vitro, and suppress formation of arteriosclerotic lesion in apoE KO mouse (see, WO2003/086437), as well as improve blood pressure or pulse wave of KHC rabbit, which is an atherosclerosis model, or human volunteers (see, WO2007/032551). The Hydroxycinnamic acid serotoninamide (serotonin derivative) contained in the extract is considered to be at least one of the anti-arteriosclerotic active forms in apoE KO mouse (see, WO2003/086437). As the serotonin derivative in a safflower seed, four kinds of N-(p-Coumaroyl)serotonin (CS), N-Feruroyl serotonin (FS) and glycosides thereof are mainly known, and the structures of these compounds are completely different from that of the NF-κB suppressant shown in the above-mentioned Martinez-Florez S et al., J. Nutr. 135:1359-1365 (2005); Yeh C-H et al., J. Surgical Res. 125:109-116 (2005); Lin C-M et al., Planta Medica 71:748-753 (2005); Gerritsen M E et al., Am. J. Pathol. 147:278-292 (1995); and Packer L, Book of abstracts, 219th ACS National Meeting, San Francisco, Calif., Mar. 26-30, (2000). CS and FS are both shown to have almost the same level of antioxidant activity (DPPH radical scavenging activity, LDL oxidation suppressive action and the like). Of these, CS is reported by Kawashima et al. to suppress production of inflammatory cytokines such as TNF-αc, IL-1, IL-6 and the like in human peripheral blood monocyte stimulated by lipopolysaccharide (LPS) of bacterium (see, Kawashima S et al., J. Interferon Cytokine Res. 18:423-428 (1998)). According to this report, CS inhibited production of TNF-α, IL-1α, IL-1β and IL-6 at a transcription level at a concentration of 50 μM or above, and inhibition of NF-κB activation was confirmed from the results of EMSA (Electrophoretic Mobility Shift Assay). However, in the follow-up report by the same research group (see, Takii T et al., Int. Immunopharmacol. 3:273-277 (2003)), it is observed that the above-mentioned effect of CS is not specific to inflammatory cytokines, but results from a non-specific protein synthesis inhibitory action and an anti-oxidant action of CS in peripheral blood-derived monocyte. Taking together all these findings, the effect of a serotonin derivative on the expression of inflammatory cytokines or NF-κB activity in a cell other than peripheral blood monocyte is unknown.

Thus, there remains a need for agents and methods for treating inflammation.

SUMMARY OF THE INVENTION

Accordingly, it is one object of the present invention to provide novel methods of improving or preventing various conditions through suppression of the expression of inflammatory cytokines based on the action mechanism of suppression of NF-κB activation.

It is another object of the present invention to provide novel methods of treating and/or preventing an inflammatory disease.

It is another object of the present invention to provide novel agents and compositions for treating and/or preventing an inflammatory disease.

It is another object of the present invention to provide novel methods for the treatment and/or prophylaxis of a disease caused by NF-κB activation.

It is another object of the present invention to provide novel agents and compositions for the treatment and/or prophylaxis of a disease caused by NF-κB activation.

These and other objects, which will become apparent during the following detailed description, have been achieved by the inventors' discovery that serotonin derivatives, particularly feruloyl serotonin and p-coumaroyl serotonin, have a significant suppressive action on NF-κB activation in vascular endothelial cells, which resulted in the completion of the present invention. Accordingly, the present invention provides the following:

(1) A composition for suppressing NF-κB activation, comprising a serotonin derivative.

(2) The composition of the aforementioned (1), wherein the aforementioned serotonin derivative is feruloyl serotonin and p-coumaroyl serotonin.

(3) The composition of the aforementioned (1), wherein the aforementioned serotonin derivative is feruloyl serotonin.

(4) The composition of the aforementioned (1), wherein the aforementioned serotonin derivative is p-coumaroyl serotonin.

(5) The composition of any of the aforementioned (1) to (4), wherein the aforementioned serotonin derivative is extracted from a plant.

(6) The composition of the aforementioned (1), wherein the aforementioned plant is a safflower seed.

(7) The composition of any of the aforementioned (1) to (6), which is a pharmaceutical agent.

(8) The composition of the aforementioned (7), which is used for the treatment or prophylaxis of a disease caused by NF-κB activation.

(9) The composition of any of the aforementioned (1) to (6), which is a food.

(10) The composition of the aforementioned (9), wherein the food is a food with health claims or a dietary supplement.

(11) The composition of the aforementioned (10), wherein the food with health claims is a food for specified health uses or a food with nutrient function claims.

(12) A method of suppressing NF-κB activation in a subject, comprising administering the composition of the aforementioned (7) or (8) to the subject in need thereof.

(13) Use of a serotonin derivative for the production of a composition for suppressing NF-κB activation.

(14) The use of the aforementioned (13), wherein the aforementioned serotonin derivative is feruloyl serotonin and p-coumaroyl serotonin.

(15) The use of the aforementioned (13), wherein the aforementioned serotonin derivative is feruloyl serotonin.

(16) The use of the aforementioned (13), wherein the aforementioned serotonin derivative is p-coumaroyl serotonin.

(17) The use of any of the aforementioned (13) to (16), wherein the aforementioned serotonin derivative is extracted from a plant.

(18) The use of the aforementioned (17), wherein the aforementioned plant is a safflower seed.

(19) A commercial package comprising the composition of the aforementioned (7) or (8) and a written matter stating that the composition can or should be used for the treatment or prophylaxis of a disease caused by NF-κB activation.

(20) The composition of the aforementioned (10) or (11), having an indication that it is used for the treatment or improvement of a state caused by NF-κB activation.

(21) A composition for suppressing the expression of VCAM-1 and/or MCP-1 via NF-κB, comprising a serotonin derivative.

(22) The composition of the aforementioned (21), wherein the aforementioned serotonin derivative is feruloyl serotonin and p-coumaroyl serotonin.

(23) The composition of the aforementioned (21), wherein the aforementioned serotonin derivative is feruloyl serotonin.

(24) The composition of the aforementioned (21), wherein the aforementioned serotonin derivative is p-coumaroyl serotonin.

(25) The composition of any of the aforementioned (21) to (24), wherein the aforementioned serotonin derivative is extracted from a plant.

(26) The composition of the aforementioned (25), wherein the aforementioned plant is a safflower seed.

(27) The composition of any of the aforementioned (21) to (26), which is a pharmaceutical agent.

(28) The composition of the aforementioned (27), which is used for the treatment or prophylaxis of a disease caused by the expression of VCAM-1 and/or MCP-1 via NF-κB.

(29) The composition of any of the aforementioned (21) to (26), which is a food.

(30) The composition of the aforementioned (29), wherein the food is a food with health claims or a dietary supplement.

(31) The composition of the aforementioned (30), wherein the food with health claims is a food for specified health uses or a food with nutrient function claims.

(32) A method of suppressing the expression of VCAM-1 and/or MCP-1 via NF-κB in a subject, comprising administering the composition of the aforementioned (27) or (28) to the subject in need thereof.

(33) Use of a serotonin derivative for the production of a composition for suppressing the expression of VCAM-1 and/or MCP-1 via NF-κB.

(34) The use of the aforementioned (33), wherein the aforementioned serotonin derivative is feruloyl serotonin and p-coumaroyl serotonin.

(35) The use of the aforementioned (33), wherein the aforementioned serotonin derivative is feruloyl serotonin.

(36) The use of the aforementioned (33), wherein the aforementioned serotonin derivative is p-coumaroyl serotonin.

(37) The use of any of the aforementioned (33) to (36), wherein the aforementioned serotonin derivative is extracted from a plant.

(38) The use of the aforementioned (37), wherein the aforementioned plant is a safflower seed.

(39) A commercial package comprising the composition of the aforementioned (27) or (28) and a written matter stating that the composition can or should be used for suppressing the expression of VCAM-1 and/or MCP-1 via NF-κB.

(40) The composition of the aforementioned (30) or (31), having an indication that it is used for the prophylaxis or improvement of a state caused by the expression of VCAM-1 and/or MCP-1 via NF-κB.

(41) An anti-inflammatory composition comprising a serotonin derivative.

(42) The composition of the aforementioned (41), wherein the aforementioned serotonin derivative is feruloyl serotonin and p-coumaroyl serotonin.

(43) The composition of the aforementioned (41), wherein the aforementioned serotonin derivative is feruloyl serotonin.

(44) The composition of the aforementioned (41), wherein the aforementioned serotonin derivative is p-coumaroyl serotonin.

(45) The composition of any of the aforementioned (41) to (44), wherein the aforementioned serotonin derivative is extracted from a plant.

(46) The composition of the aforementioned (45), wherein the aforementioned plant is a safflower seed.

(47) The composition of any of the aforementioned (41) to (46), which is a pharmaceutical agent.

(48) The composition of the aforementioned (47), which is used for the treatment or prophylaxis of an inflammatory bowel disease.

(49) The composition of any of the aforementioned (41) to (46), which is a food.

(50) The composition of the aforementioned (49), wherein the food is a food with health claims or a dietary supplement.

(51) The composition of the aforementioned (50), wherein the food with health claims is a food for specified health uses or a food with nutrient function claims.

(52) A method of treating or preventing an inflammatory disease in a subject, comprising administering the composition of the aforementioned (47) or (48) to the subject in need thereof.

(53) Use of a serotonin derivative for the production of a composition for anti-inflammation.

(54) The use of the aforementioned (53), wherein the aforementioned serotonin derivative is feruloyl serotonin and p-coumaroyl serotonin.

(55) The use of the aforementioned (53), wherein the aforementioned serotonin derivative is feruloyl serotonin.

(56) The use of the aforementioned (53), wherein the aforementioned serotonin derivative is p-coumaroyl serotonin.

(57) The use of any of the aforementioned (53) to (56), wherein the aforementioned serotonin derivative is extracted from a plant.

(58) The use of the aforementioned (57), wherein the aforementioned plant is a safflower seed.

(59) A commercial package comprising the composition of the aforementioned (47) or (48) and a written matter stating that the composition can or should be used for the treatment or prophylaxis of an inflammatory disease.

(60) The composition of the aforementioned (50) or (51), having an indication that it is used for the prophylaxis or improvement of an inflammatory disease.

(61) An agent for suppressing NF-κB activation, comprising a serotonin derivative.

(62) The suppressant of the aforementioned (61), wherein the aforementioned serotonin derivative is feruloyl serotonin and p-coumaroyl serotonin.

(63) The suppressant of the aforementioned (61), wherein the aforementioned serotonin derivative is feruloyl serotonin.

(64) The suppressant of the aforementioned (61), wherein the aforementioned serotonin derivative is p-coumaroyl serotonin.

(65) The suppressant of any of the aforementioned (61) to (64), wherein the aforementioned serotonin derivative is extracted from a plant.

(66) The suppressant of the aforementioned (65), wherein the aforementioned plant is a safflower seed.

(67) An agent for suppressing the expression of VCAM-1 and/or MCP-1 via NF-κB, comprising a serotonin derivative.

(68) The suppressant of the aforementioned (67), wherein the aforementioned serotonin derivative is feruloyl serotonin and p-coumaroyl serotonin.

(69) The suppressant of the aforementioned (67), wherein the aforementioned serotonin derivative is feruloyl serotonin.

(70) The suppressant of the aforementioned (67), wherein the aforementioned serotonin derivative is p-coumaroyl serotonin.

(71) The suppressant of any of the aforementioned (67) to (70), wherein the aforementioned serotonin derivative is extracted from a plant.

(72) The suppressant of the aforementioned (71), wherein the aforementioned plant is a safflower seed.

(73) An anti-inflammatory agent comprising a serotonin derivative.

(74) The agent of the aforementioned (73), wherein the aforementioned serotonin derivative is feruloyl serotonin and p-coumaroyl serotonin.

(75) The agent of the aforementioned (73), wherein the aforementioned serotonin derivative is feruloyl serotonin.

(76) The agent of the aforementioned (73), wherein the aforementioned serotonin derivative is p-coumaroyl serotonin.

(77) The agent of any of the aforementioned (73) to (76), wherein the aforementioned serotonin derivative is extracted from a plant.

(78) The agent of the aforementioned (77), wherein the aforementioned plant is a safflower seed.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
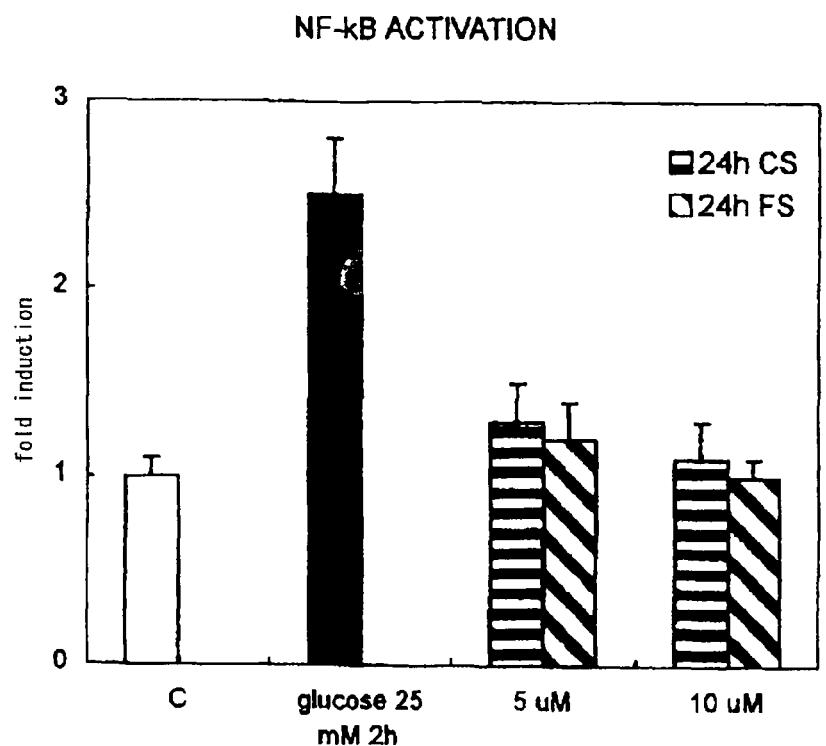
FIG. 1 is a graph showing the investigation results of the effect of a serotonin derivative on the activation of NF-κB in human aortic endothelial cells.

The present invention relates to compositions for suppressing NF-κB activation, comprising a serotonin derivative as an active ingredient. As stated in the Discussion of the Background, production of various inflammatory mediators (inflammatory cytokines, adhesion molecules, leukocyte chemotactic factors, prostaglandins and the like) is involved in the process of the onset and aggravation of inflammatory diseases. Many of the genes involved in the production of these inflammatory mediators are known to have a common process of NF-κB activation in the expression process thereof. In addition, HIV, HTLV-1, cytomegalovirus and the like require activation of NF-κB in the self-replicating process. Moreover, activation of NF-κB is also involved in the induction of the expression of various cytokines. Therefore, a substance that suppresses activation of NF-κB has a potential for suppression of the onset and progression of many inflammatory diseases, virus infections, tumor metastasis, immune diseases, and the like.

Examples of the inflammatory disease include myocardial infarction, viral encephalitis, arthritis (chronic rheumatoid arthritis, osteoarthritis and the like), psoriasis, inflammatory bowel disease, lung hypertension, sepsis, type II diabetes, hepatic fibrosis, nephrosclerosis, endometriosis, and the like.

Examples of the virus infection include AIDS, adult T cell leukemia, herpesvirus, EB virus, and the like.

Examples of the tumor metastasis include metastasis of malignant tumors (melanoma, colorectal cancer, breast cancer, etc.).

Examples of the immune disease include allergy (bronchial asthma, allergic rhinitis, and the like), allogeneic transplantation rejection, and the like.

The present invention provides a method using a serotonin derivative for preventing, improving or treating the above-mentioned diseases and disorders in which activation of NF-κB is considered to be deeply involved. However, the diseases and disorders responsive to the activation of NF-κB are not limited to those recited above. The serotonin derivative in the context of the present specification and claims is a concept including salts acceptable for product formulation. Examples of the salt include acid addition salt, for example, inorganic acid addition salts (hydrochloride, hydrogen bromide, sulfate, phosphate, and the like), organic acid addition salts (formate, acetate, trifluoroacetate, maleate, tartrate, methanesulfonate, benzenesulfonate, toluenesulfonate, and the like), salts with amino acid (aspartate, glutamate, and the like), metal salts, for example, alkali metal salts (sodium salt, potassium salt, and the like), alkaline earth metal salts (calcium salt, magnesium salt, and the like) and the like.

In the present invention, the term "suppression of NF-κB activation" means suppression of the translocation of NF-κB into the nucleus. The suppression of the translocation of NF-κB into the nucleus can be confirmed by the method described in Example 1. To be specific, a test substance is added to a culture medium of human aortic endothelial cells, the cells are incubated for a predetermined time, the nucleus is extracted from the aforementioned cells stimulated with glucose, and activated NF-κB (p65) translocated into the nucleus is detected. Using the cells before glucose stimulation, wherein NF-κB is not activated, as a negative control and the cells stimulated with glucose and free of addition of a test substance as a positive control, when the detection level of the aforementioned p65 is closer to the negative control than to the positive control, NF-κB activation is evaluated to have been suppressed.

Examples of the serotonin derivative contained in the composition for suppressing NF-κB activation of the present invention include a compound (I) represented by the following formula.

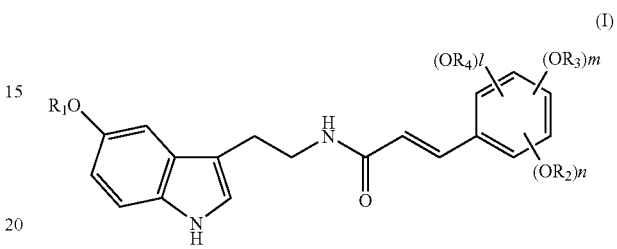

(I)

wherein $R_1$, $R_2$, $R_3$, and $R_4$ are each independently a hydrogen atom, an alkyl group having a carbon number of 1 to 3, or a sugar, and n, m, and l are each 0 or 1. In the present specification, examples of the alkyl group having a carbon number of 1 to 3 include methyl, ethyl, n-propyl and i-propyl. Examples of the sugar include glucose, mannose, galactose, fucose, rhamnose, arabinose, xylose, fructose, rutinose, galacturonic acid, glucuronic acid, neohesperidose and the like. Examples of the preferable compound include serotonin hydroxycinnamide.

Preferable examples of hydroxycinnamic acid include p-coumaric acid, ferulic acid, and caffeic acid. Examples of serotonin amide thereof include N-(p-coumaroyl)serotonin (or p-coumarilic serotonin or p-coumaroyl serotonin), N-feruloyl serotonin (or ferulyl serotonin or feruloyl serotonin) and caffeoyl serotonin.

The serotonin derivative to be used in the present invention may be a glycoside. Here, examples of the aforementioned glycoside of serotonin derivative include, but are not limited to, O-β-D-glucopyranoside wherein β-glucoside linkage is formed between glucose for $R_1$ and compound (I), and the like.

As the serotonin derivative, one kind of the above-mentioned compound can be used alone, or two or more kinds of compounds can be used in combination.

A serotonin derivative can be prepared by chemical synthesis or extraction from a naturally occurring substance.

The compound is known per se, and can be synthesized by a method known per se. Preferable specific examples include the method described in the below-mentioned Experimental Example 1.

When a serotonin derivative is extracted from a naturally occurring substance, various plant tissues can be used as starting materials. For example, a seed of Asteraceae plants such as safflower and knapweed, kernel and plant tuber of Japanese barnyard millet, elephant foot, and the like, and the like can be mentioned, with preference given to safflower seed and defatted grounds thereof. In the present invention, the plant seed may be the whole constituting the plant seed, a part thereof, for example, seed coat, endosperm, germ and the like taken out therefrom, or a mixture thereof. As an extraction method from these, for example, the following methods can be mentioned.

Plant tissues are generally subjected to extraction as defatted material (meal). Defatted material can be obtained by a method known per se, such as defatting plant tissues (e.g., plant seeds). For example, it can be obtained by press-extracting seeds, or extracting crushed seeds with n-hexane and the like, then separating a solid content from the extraction system, and drying the solid content. A rough level of defatting is generally not less than 60 wt %, preferably not less than 80 wt %.

An example of the extraction method includes washing the following defatted plant seeds, which is a starting material, with water, and extracting them with an organic solvent.

Water is not particularly limited. For example, all of distilled water, tap water, industrial water, a mixture of these and the like can be used. Water may contain other substances, such as inorganic salts (e.g., sodium chloride, potassium chloride, calcium chloride etc.), acid (e.g., hydrogen chloride, acetic acid, carbonic acid, hydrogen peroxide, phosphoric acid etc.), alkali (e.g., sodium hydroxide, potassium hydroxide, sodium hydrogencarbonate etc.) and the like, as long as the effect of the present invention can be afforded. During washing, the pH is generally 2 to 9, preferably 5 to 7.

The total amount of water to be used is generally 2- to 100-fold amount (water volume/defatted plant seed weight, hereinafter the same), preferably 10- to 40-fold amount, relative to the defatted plant seed (starting material).

For washing, a defatted plant seed (starting material) is brought into contact with water by a method known per se. For example, a method in which a defatted plant seed is suspended in water, filtered, and the solid after washing treatment is recovered, and the like can be used. For washing, water in the above-mentioned amount may be brought into contact with defatted plant seed once or in a plurality of times, or continuously. The temperature during contact is generally 5 to 45° C., preferably 25 to 35° C. The contact time is generally 10 to 240 minutes, preferably 15 to 60 minutes.

The defatted plant seed and the like obtained after a washing treatment as mentioned above can be extracted with an organic solvent to give an extract of the plant seed and the like.

Examples of the organic solvent include, but are not limited to, lower alcohol, acetone, acetonitrile and a mixed solvent thereof and the like. The organic solvent may or may not contain water. The concentration of the organic solvent is generally 20 to 95 wt %, preferably 50 to 90 wt %. In consideration of concentration, drying and food production of an extract after extraction, the organic solvent is preferably lower alcohol. Examples of the lower alcohol include, but are not limited to, alcohol having 1 to 4 carbon atoms, specifically methanol, ethanol, n-propanol, isopropanol, n-butanol, and the like. From the aspects of food production, the lower alcohol is preferably ethanol. The ethanol is preferably water-containing ethanol having an ethanol content of not less than 50 wt % or anhydrous ethanol.

The amount of the organic solvent to be used is generally a 2- to 40-fold amount (organic solvent volume/defatted plant seed weight, hereinafter the same), preferably 2- to 10-fold amount, relative to the defatted plant seed (starting material). The extraction temperature is generally 20 to 75° C., preferably 50 to 70° C. The extraction time is generally 10 to 240 minutes, preferably 60 to 120 minutes.

After extraction, the solid content is separated from the suspension by filtration or the like, and the obtained extract may be used as it is or, where necessary, used after concentration and drying, as the plant seed extract of the present invention. For concentration and drying, the extract may be concentrated or dried as it is, or may be concentrated or dried after addition of an excipient (e.g., lactose, sucrose, starch, cyclodextrin, etc.). While the extract obtained by extraction with the above-mentioned solvent may be used in the present invention at that purity, it may be further purified according to a method known per se.

One example for further increasing the purity is described, but the method is not limited thereto. The organic solvent of the aforementioned solvent extract is evaporated under reduced pressure; water is added thereto; the extract is suspended in the water; the aqueous phase is washed with a nonpolar solvent, for example, n-hexane, n-heptane, n-octane or the like, preferably n-hexane; and the aqueous layer after washing is extracted with a solvent that can extract the desired composition by separating the aqueous layer into two layers, such as acetate, n-butanol or the like, preferably ethyl acetate, methyl acetate, propyl acetate, etc. Then, the extract is washed with saturated brine or the like to obtain an organic layer. When extracted with acetate ester, the organic layer is dehydrated with, for example, anhydrous magnesium sulfate or the like and then concentrated under reduced pressure to give a solid (composition). Purification may be ceased at any stage mentioned above, any step may be omitted or modified, and additional purification may be performed. Including changing the kind of the above-mentioned solvent, a multi-step extraction method, a countercurrent distribution method and the like may also be used.

The serotonin derivative to be used in the present invention, inter alia, N-(p-coumaroyl)serotonin and N-feruloyl serotonin, suppresses intracellular oxidative stress, whereby activation of NF-κB is suppressed, and translocation thereof into the nucleus is suppressed. As a result, the expression of VCAM-1, MCP-1 gene, and the like, which are under the control of NF-κB, is suppressed at the transcription level and excessive production of gene products thereof is suppressed, whereby it is considered that an anti-inflammatory action is performed. N-(p-coumaroyl)serotonin (p-coumaroyl serotonin) and N-feruloyl serotonin (feruloyl serotonin) are represented by the following structural formulas.

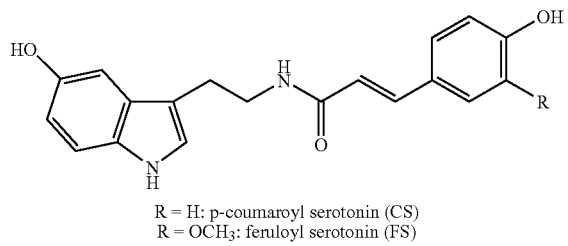

R = H: p-coumaroyl serotonin (CS)
R = OCH$_3$: feruloyl serotonin (FS)

In another aspect, the present invention also relates to a composition for suppressing the expression of VCAM-1 and/or MCP-1 via NF-κB, comprising a serotonin derivative. The composition is expected to achieve improvement or prophylaxis of the aforementioned many inflammatory diseases, virus infections, tumor metastasis, immune diseases, inter alia, intractable inflammatory immune diseases such as inflammatory bowel disease, pulmonary hypertension, rheumatoid arthritis, hepatofibrosis and the like, atherosclerosis after organ transplantation, nephrosclerosis, endometriosis, bronchial asthma or allergic rhinitis.

The composition of the present invention contains the aforementioned serotonin derivative as an active ingredient, and also contains an excipient (e.g., lactose, sucrose, starch, cyclodextrin etc.) and, when demanded, flavor, dye, seasoning, stabilizer, preservative and the like, and can be used as a food (food composition) or a pharmaceutical preparation (pharmaceutical composition), by formulating a preparation in the form of tablet, pill, granules, fine granules, powder, pellet, capsule, solution, emulsion, suspension, syrup, troche, and the like.

While the amount of the serotonin derivative contained in the composition of the present invention is not particularly limited as long as the effect of the invention is afforded, it is generally 0.0001 to 99.9 wt %, preferably 0.001 to 99.5 wt %, more preferably 0.005 to 99 wt %.

Particularly, when used as a pharmaceutical agent, the derivative can be formulated into a preparation together with a carrier (including additives) acceptable as a pharmaceutical agent. Examples of the pharmaceutically acceptable carrier include, but are not limited to, excipient (e.g., lactose, sucrose, dextrin, hydroxypropylcellulose, polyvinylpyrrolidone etc.), disintegrant (e.g., starch, carboxymethylcellulose etc.), lubricant (e.g., magnesium stearate etc.), surfactant (e.g., sodium lauryl sulfate etc.), solvent (e.g., water, brine, soybean oil etc.), preservative (e.g., p-hydroxybenzoate etc.) and the like.

While the "food" of the present invention refers to food in general, it also means general foods (so-called health food), as well as food with health claims provided in the food with health claims system of The Japanese Ministry of Health, Labor and Welfare, such as food for specified health uses and food with nutrient function claims and the like. Furthermore, the food of the present invention encompasses dietary supplements (supplement, nutritional supplement), feed, food additive and the like.

For food uses, a serotonin derivative can also be used, for example, by adding to general foods (inclusive of so-called health food) such as dressing, mayonnaise and the like. In addition, a serotonin derivative can be formulated into a tablet, pill, granule, fine granule, powder, pellet, capsule, solution, emulsion, suspension, syrup, troche and the like, together with an excipient (e.g., lactose, sucrose, starch etc.), and in some cases, flavor, dye etc., and used as a food with health claims such as a food for specified health uses, a food with nutrient function claims and the like, or as a supplement. Moreover, the composition of the present invention can be applied to feed uses, and can be ingested by or administered to poultry, domestic animals and the like by addition to general feed.

The composition of the present invention for suppressing NF-κB activation is preferably used as a food for specified health uses or a food with nutrient function claims in order to effectively exhibit the biological action of the contained serotonin derivative. In this case, it is recommended to attach an indication stating, "it is used for the prophylaxis or improvement of the condition caused by NF-κB activation".

The composition of the present invention for suppressing expression of VCAM-1 and/or MCP-1 is preferably used as a food for specified health uses or a food with nutrient function claims in order to effectively exhibit the biological action of the contained serotonin derivative. In this case, it is recommended to attach an indication stating, "it is used for the improvement or prophylaxis of a disease caused by expression of VCAM-1 and/or MCP-1 via NF-κB".

The composition of the present invention for anti-inflammation is preferably used as a food for specified health uses or a food with nutrient function claims in order to effectively exhibit the biological action of the contained serotonin derivative. In this case, it is recommended to attach an indication stating, "it is used for the improvement or prophylaxis of an inflammatory disease".

The subject of the composition of the present invention is an animal including human (mammals such as human, bovine, swine, dog, cat and the like, birds such as chicken and the like etc.). The target cell of the composition of the present invention is not particularly limited as long as it is other than monocyte, and examples of preferable cell include cells wherein VCAM-1 and/or MCP-1 are/is highly expressed, specifically, vascular endothelial cells, vascular smooth muscle cells and renal glomerulus cells. The target effector cell of the composition of the present invention includes granulocytes such as monocyte, macrophage, neutrophil, eosinophil, basophil and the like, lymphocytes such as killer T cell and the like, natural killer cell, mast cell, dendritic cell and the like.

The method of ingestion or administration of the composition of the present invention varies depending on the age, body weight and health condition of the ingestion or administration subject. When, for example, maintenance or enhancement of health or prophylaxis of diseases is desired, the composition is generally administered orally in the form of a food. When treatment of diseases or recovery of health is desired, the composition is generally administered orally in the form of a pharmaceutical product or food, or administered as an injection, external preparation and the like. When a synthesized serotonin derivative is to be administered, a daily dose of 0.2 mg to 2 g, preferably 20 mg to 2 g, is preferably ingested by or administered to an adult in one to several portions a day. When the safflower seed extract of Example 6 or Example 8 is orally ingested, a daily dose of 1 mg to 10 g, preferably 100 mg to 10 g, is preferably ingested by or administered to an adult in one to several portions a day. In this case, a daily ingestion amount or an ingestion amount per administration can be packaged as one unit.

The serotonin derivative contained in the composition of the present invention preferably maintains a given level of blood concentration for a given period of time after ingestion by or administration to an animal as mentioned above. While the blood concentration is not particularly limited as long as the effect of the invention can be afforded, it is generally less than 50 μM, and recommended to be preferably 0.1 to 10,000 nM, more preferably 1-5,000 nM, still more preferably 100-1,000 nM.

The serotonin derivative is contained in various plant seeds, plant tubers and the like, and particularly contained in a large amount in safflower seeds. In Korea, since safflower seeds have been used for promoted cure of bone fracture, prevention of osteoporosis and the like among the people since ancient times, its safety is considered to be high. The results of Example 9 described below have also established that the composition of the present invention has low-toxicity and hardly causes adverse effects.

Other features of the invention will become apparent in the course of the following descriptions of exemplary embodiments which are given for illustration of the invention and are not intended to be limiting thereof.

EXAMPLES

Experimental Example 1

Synthesis of Serotonin Derivative p-Coumaroyl serotonin (CS) and feruloyl serotonin (FS) were synthesized by the following method.

CS: serotonin hydrochloride was dissolved in dimethylformamide (5 mL/g vs. serotonin hydrochloride, hereinafter the same) and dichloromethane (20 mL/g), 1.1 equivalents each of trans-4-coumaric acid (1.0 mol/mol), 1-hydroxybenzotriazole hydrate (HOBt), 1-[3-(dimethylamino)propyl]-ethylcarbodiimide hydrochloride (EDC), and triethylamine were added, and the mixture was reacted with stirring at room temperature overnight. The reaction mixture was concentrated under reduced pressure, ethyl acetate and water (each 40 mL/g serotonin) were added, and the mixture was extracted with ethyl acetate. The extraction phase obtained by 3 times of ethyl acetate extraction was washed successively with 5% aqueous citric acid solution, saturated aqueous sodium hydrogencarbonate solution, and saturated brine, and dried over anhydrous sodium sulfate. The desiccant was removed and the resulting extract was concentrated under reduced pressure. The residue was crystallized from ethyl acetate-ethanol (10:0.6) and the obtained crystals were washed with ethyl acetate and dried to give CS (yield=69.8%).

FS: Synthesized from serotonin hydrochloride and trans-4-ferulic acid in the same manner as above for CS except that the crystallization was performed using methanol-chloroform (1:15) (yield=69.2%).

Example 1

Action of Serotonin Derivatives (CS, FS) on Activation of NF-κB

Human aortic endothelial cells (HAEC) were purchased from Clonetics Corp, and the cells cultured for 3-4 passages (37° C., under 5% carbon dioxide gas atmosphere) were used for the experiment. After pre-incubation with CS and FS (5 and 10 μM each) in a culture dish (100 mmϕ) for 24 hours, the cells were stimulated with 25 mM glucose for 2 hours. Nucleus was extracted from the cells using Nuclear Extract Kit (Active Motif), and then the activated NF-κB (p65) translocated into the nucleus was detected by TransAM NF-κB p65 Kit (Active Motif).

As shown in FIG. 1, the treatment with high concentration glucose for 2 hours remarkably increased the nuclear translocation of p65 and marked activation of NF-κB was observed. However, the pre-treatment with 5 and 10 μM of CS or FS significantly suppressed the nuclear translocation of p65. Therefrom it was shown that the serotonin derivative suppresses the activation of NF-κB in human aortic endothelial cells.

Figure 2:
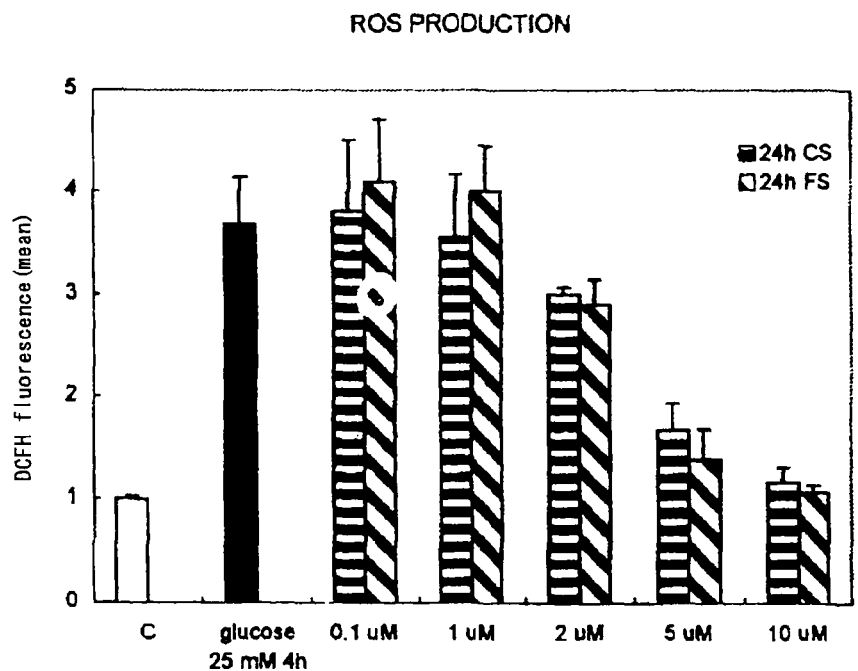
FIG. 2 is a graph showing the investigation results that a serotonin derivative lowers an increase in the ROS production in a dose-dependent manner in human aortic endothelial cells.

To examine the suppressive mechanism of NF-κB activation, HAEC cells pre-treated with the serotonin derivative as mentioned above were stimulated with 25 mM glucose for 1 hour and then the fluorescence intensity based on the production of intracellular reactive oxygen species (ROS) was measured according to the method of Takahashi M et al., Free Radic. Biol. Med. 31:164-174 (2001). It was found that the serotonin derivative dose-dependently reduces ROS production increased by stimulation with high concentration glucose (FIG. 2). Therefrom it was shown that the serotonin derivative suppresses NF-κB activation and the subsequent nuclear translocation of NF-κB by suppressing the intracellular oxidation stress.

Example 2

Action of Serotonin Derivative (CS, FS) on Gene Expressions of VCAM-1 and MCP-1

HAEC cells pre-treated with 10 μM of CS or FS for 24 hours were stimulated with 25 mM glucose for 3 hours, and total RNA was extracted with Isogenkit (NIPPON GENE CO., LTD.). From 1 μg of RNA, cDNA was synthesized using 100 U/mL of reverse transcriptase (TAKARA BIO INC.) and 0.1 μM of oligo (dT)-adapter (TAKARA BIO INC.) (total volume of reaction mixture; 50 μL) (42° C., 40 minutes). Real-time PCR was performed using 7300 Real Time PCR system (Applied Biosystems Japan Ltd.) and the PCR product was detected by SYBER Green I.

PCR reaction composition (RT-PCRkit, TAKARA BIO INC.): 12.5 μL Premix Ex Taq, 2.5 μL SYBER Green I, synthesis primer, ROX reference dye, cDNA (corresponding to 20 ng of total RNA), final reaction volume; 25 μL Primers having the following sequences were used.

```
detection of VCAM-1 gene:
                                        (SEQ ID NO: 1)
5'-CCCTTGACCGGCTGGAGATT-3'              (sense)

(SEQ ID NO: 2)
5'-CTGGGGGCAACATTGACATAAAGTG-3'         (antisense)

Detection of MCP-1 gene:
                                        (SEQ ID NO: 3)
5'-CGCCTCCAGCATGAAAGTCT-3'              (sense)

(SEQ ID NO: 4)
5'-GGAATGAAGGTGGCTGCTATG-3'             (antisense)

detection of GAPDH (internal standard) gene:
                                        (SEQ ID NO: 5)
5'-ACCACAGTCCATGCCATCAC-3'              (sense)

(SEQ ID NO: 6)
5'-TCCACCACCCTGTTGCTGTA-3'              (antisense)
```

PCR was conducted under the following conditions.

thermal denaturation: at 95° C. for 15 seconds, extension reaction: 40 cycles (3 seconds at 95° C., 31 seconds at 60° C.)

Expression amounts of VCAM-1 and MCP-1 mRNA were calculated using GAPDH as the internal standard.

Figure 3:
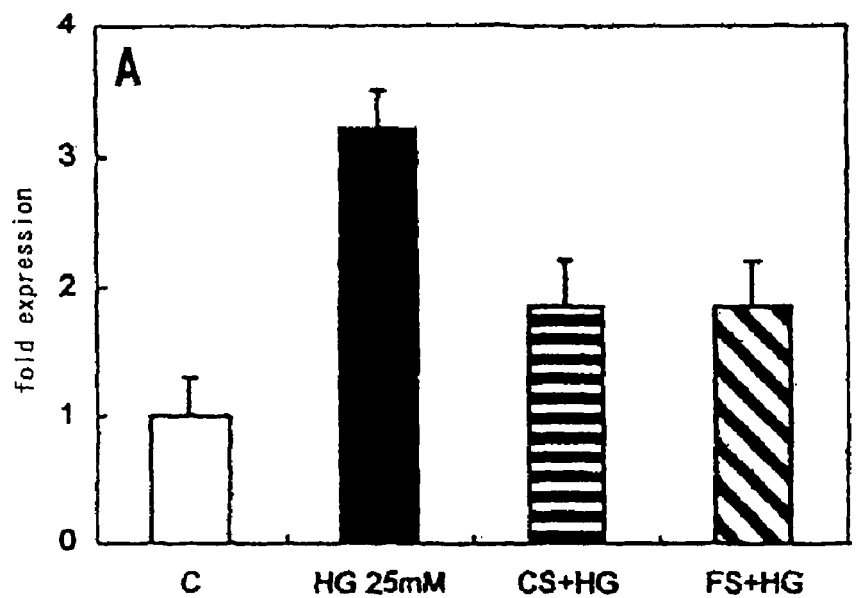
FIG. 3 presents graphs showing the investigation results by realtime PCR of the effect of a serotonin derivative on the mRNA expressions of VCAM-1(A) and MCP-1(B) in human aortic endothelial cells.
Figure 3:
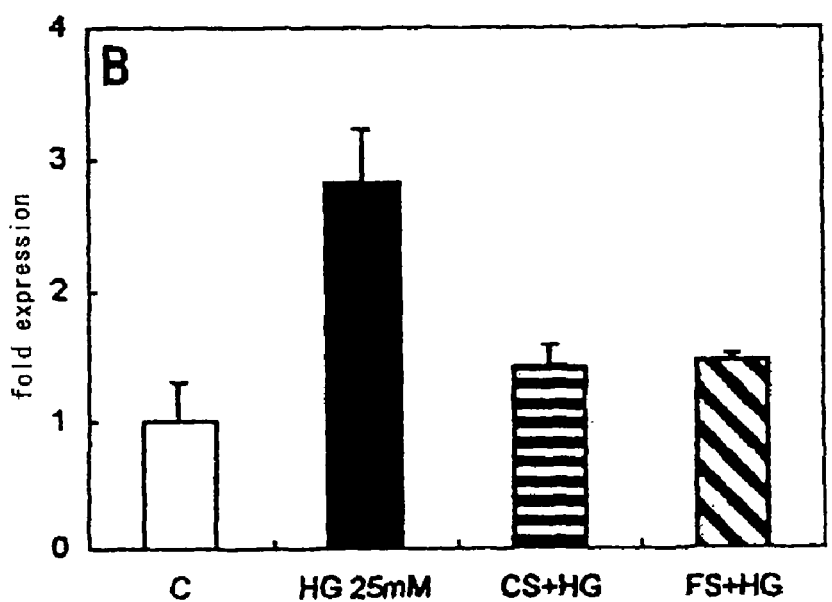

As shown in FIGS. 3A and 3B, the expression amounts of VCAM-1 and MCP-1 mRNA in HAEC cells both increased to about 3 times that of the untreated cells, by the stimulation with high concentration glucose, and both CS and FS significantly suppressed the increase. Therefrom it was shown that the serotonin derivative suppresses the expressions of VCAM-1 and MCP-1 at a transcription level in human aortic endothelial cells stimulated with high glucose. From the results of Example 1, the serotonin derivative was considered to suppress, based on suppression of NF-κB activation, transcriptions of these genes induced by high glucose stimulation.

Example 3

Action of Serotonin Derivatives (CS, FS) on Protein Expressions of VCAM-1 and MCP-1

HAEC cells proliferated to confluence in a 96 well microplate were pre-incubated with 0.1-10 μM serotonin derivative for 24 hours, and stimulated with 25 mM glucose for 4 hours. The cell layer was washed with Hanks solution, and then anti-VCAM-1 monoclonal antibody (Becton Dickinson) was added and the cells were incubated at 37° C. for 1 hour. After washing, the cells were incubated with secondary antibody (peroxidase-labeled anti-mouse IgG goat F(ab')$_2$ fragment; Cappel) for 1 hour. A color development substrate (o-phenylenediamine dihydrochloride) was added and, about 30 minutes later (room temperature), the absorbance (492 nm) of each well was quantified with a microplate reader. The MCP-1 concentration of the medium was quantified with Human MCP-1 Immunoassay Kit (BioSource International).

Figure 4:
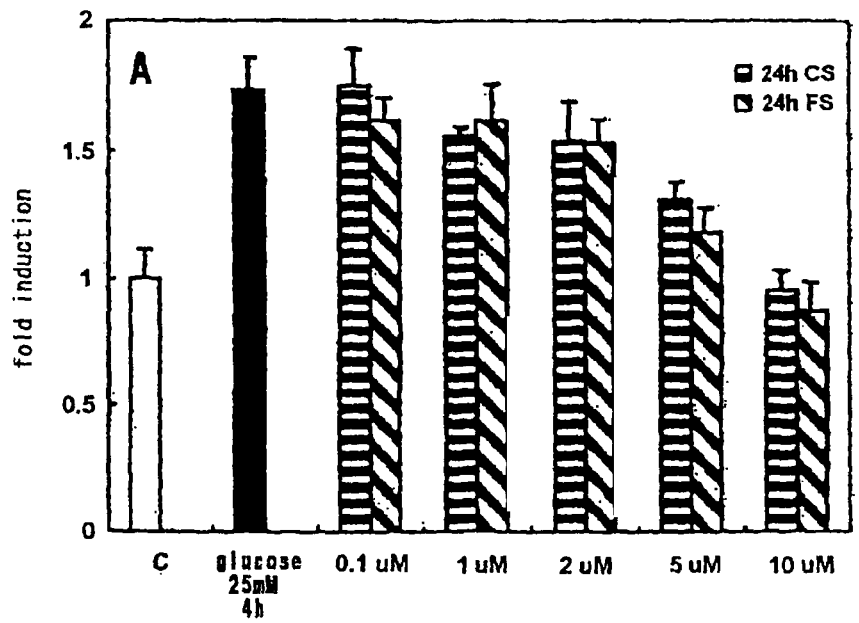
FIG. 4 presents graphs showing the investigation results based on immunostaining of the effect of a serotonin derivative on the induction of protein expressions of VCAM-1(A) and MCP-1(B) in human aortic endothelial cells.
Figure 4:
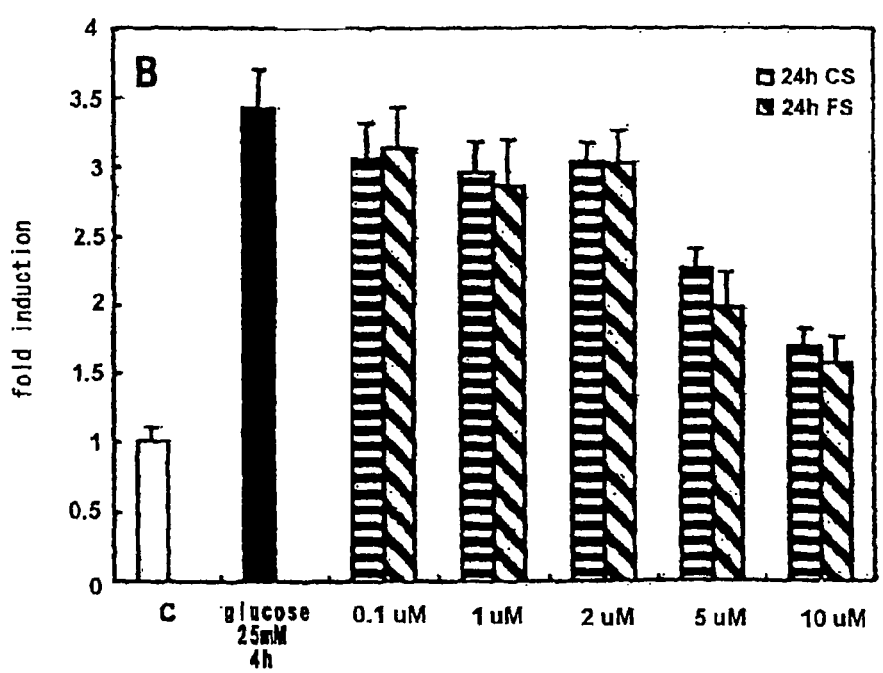

As shown in FIGS. 4A, and 4B, VCAM-1 expression on the cell membrane and MCP-1 secretion into the medium increased to a little less than 2 times and about 3.5 times that of untreated cells, respectively, by stimulation with high concentration glucose. However, both CS and FS suppressed the induction of their expressions in a dose-dependent manner. Therefrom it was shown at a protein level that a serotonin derivative suppresses the induction of expression of VCAM-1 and MCP-1 in human aortic endothelial cells stimulated with high glucose.

Example 4

Action of Serotonin Derivatives (CS, FS) on Monocyte Adhesion to HAEC Cells

HAEC cells proliferated to confluence in a 24 well microplate were pre-incubated with CS and FS (5 or 10 μM each) for 24 hours and stimulated with 25 mM glucose for 4 hours. The cell layer was washed with Hanks solution, and then a suspension ($1 \times 10^6$/mL, 200 μL) of U-937 monocyte cells (purchased from ATCC) was added, and the mixture was incubated at 37° C. for 30 minutes. After washing again, the cells were fixed with 1% para-formaldehyde and the number of U-937 cells attached onto HAEC was counted under a microscope (20 fields). The experiment was performed 3 times and the results are shown as an average value thereof. An experiment using fluorescence-labeled U-937 cells was also performed. To be specific, U-937 cells were incubated (37° C., 1 hour) in the presence of 10 μM 2',7'-bis(2-carboxyethyl)-5(6)-carboxyfluorescein acetoxymethylester (BCECF-AM, Molecular Probes) and washed by centrifugation. Fluorescence-labeled U-937 cells ($1 \times 10^6$/mL) were added to HAEC cells, and the mixture was incubated at 37° C. for 1 hour. The floating U-937 cells were removed, the plate was washed with PBS buffer and treated with 1% Triton X for 2 hours. The fluorescence amount of the attached cells was quantified (Ex. 503 nm, Em. 525 nm) using a fluorescence plate reader (Bio-Rad, Fluoromark).

Figure 5:
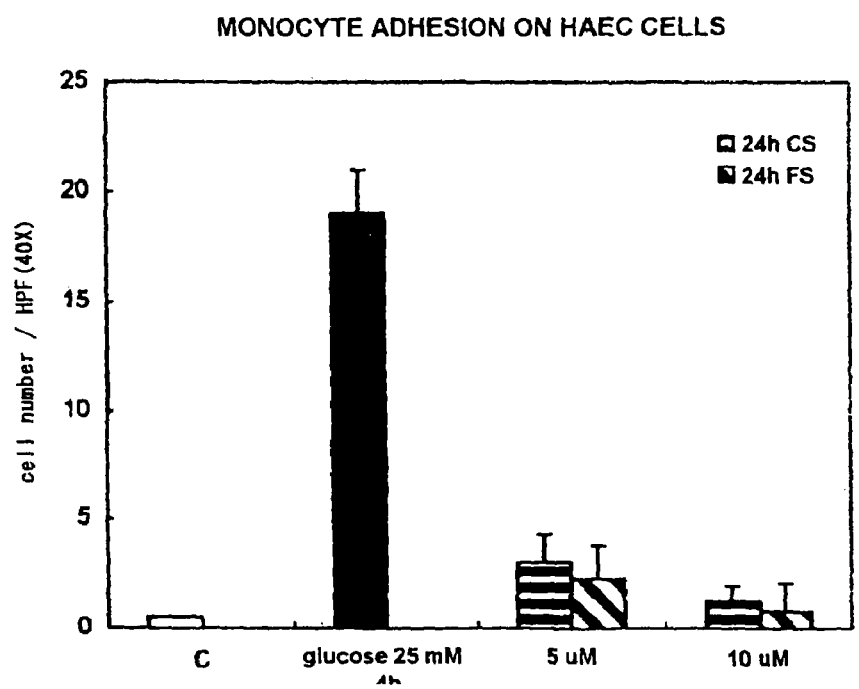
FIG. 5 is a graph showing the investigation results based on the cell count of the effect of a serotonin derivative on the adhesion of monocyte onto human aortic endothelial cells.
Figure 6:
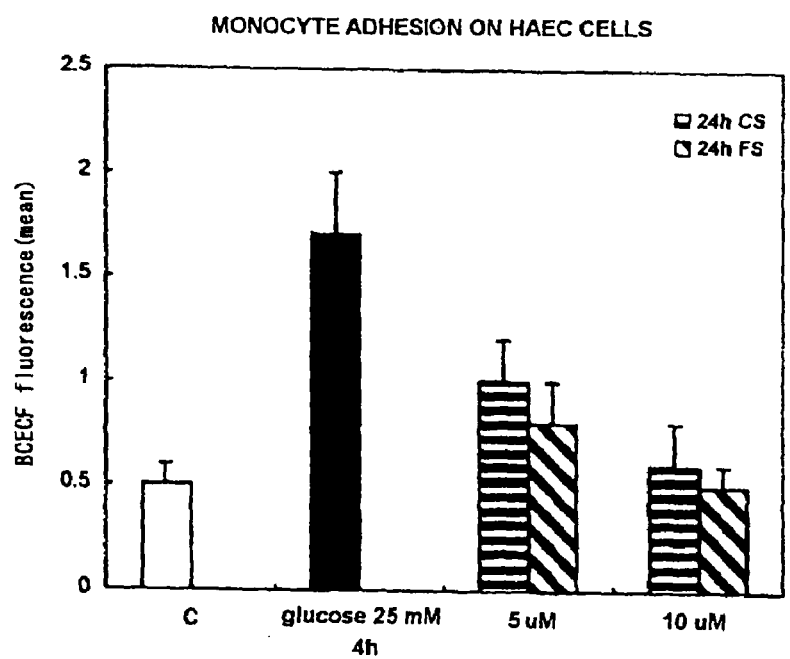
FIG. 6 is a graph showing the investigation results by fluorescence labeling of the effect of a serotonin derivative on the adhesion of monocyte onto human aortic endothelial cells.

As shown in FIG. 5, the number of U-937 cells attached onto the HAEC cells increased remarkably by stimulation with high concentration glucose. However, pre-incubation with CS or FS decreased the number of attached cells in a serotonin derivative dose-dependent manner. Similar results were also confirmed by a fluorescence intensity assay using fluorescence-labeled U-937 cells (FIG. 6). Therefrom it was shown that a serotonin derivative suppresses adhesion of monocyte to the endothelial cells induced by stimulation with high concentration glucose. The results of Example 2 and Example 3 and the adhesion of U-937 cells onto the HAEC stimulated with high concentration glucose were suppressed by the addition of anti-VCAM-1 monoclonal antibody (data not shown). From this, the suppression is considered to be attributable to the suppression of the induction of VCAM-1 expression on endothelial cells by the serotonin derivative.

Example 5

Action of Serotonin Derivatives (CS, FS) on Migration Capability of Monocyte

The migration capability of monocyte was measured using the Transwell system (pore size 3 μm; BD Biosciences). HAEC cultured on a transwell placed in a 24 well microplate was pre-incubated with 5 or 10 μM serotonin derivative for 24 hours, and stimulated with 25 mM glucose for 4 hours. 200 μL of U-937 cell suspension ($10^6$ cells/mL) was added to the transwell and the cells were incubated as-is at 37° C. for 2 hours. The number of cells migrated to the lower chamber of the transwell through the membrane was counted under a microscope (20 fields). The experiment was repeated three times, and the results are shown as an average value thereof. An experiment using fluorescence-labeled U-937 cells was also performed. BCECF-AM-labeled U-937 cells were plated in the upper chamber of the transwell and incubated at 37° C. for 2 hours. The cells migrated to the lower chamber through the membrane were collected in 1 mL of PBS buffer and treated with 1% Triton X for 2 hours. The fluorescence derived from the migrated cells was quantified (Ex. 503 nm, Em. 525 nm) using a fluorescence plate reader (Bio-Rad, Fluoromark).

After incubation (37° C., 1 hour), the cells were washed by centrifugal operation. The fluorescence-labeled U-937 cells ($1 \times 10^6$/mL) were added to HAEC cells, and the cells were incubated at 37° C. for 1 hour. The floating U-937 cells were removed, the plate was washed with PBS buffer and treated with 1% Triton X for 2 hours. The fluorescence amount of the attached cells was quantified (Ex. 503 nm, Em. 525 nm) using a fluorescence plate reader (Bio-Rad, Fluoromark).

Figure 7:
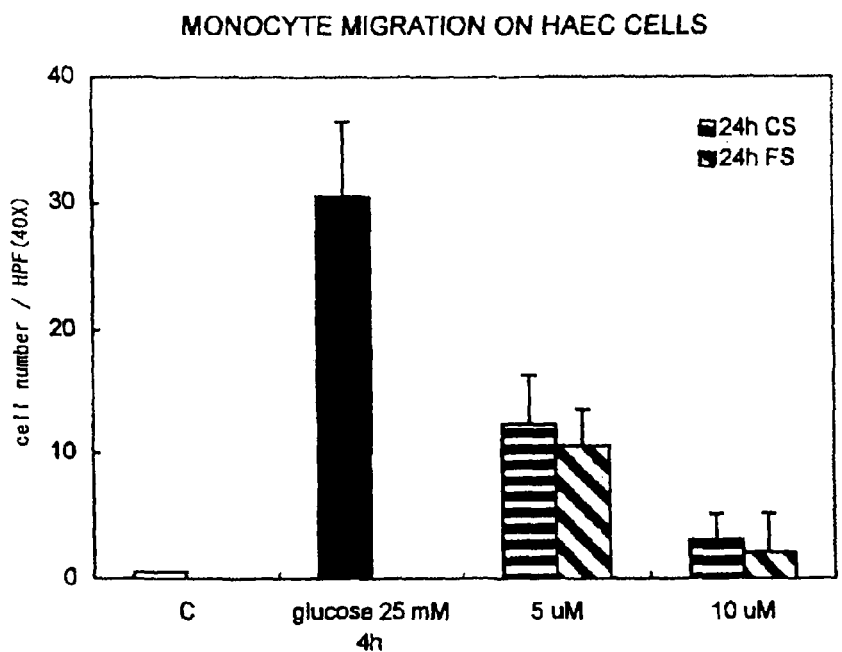
FIG. 7 is a graph showing the investigation results based on the cell count of the effect of a serotonin derivative on the migration capability of monocyte.
Figure 8:
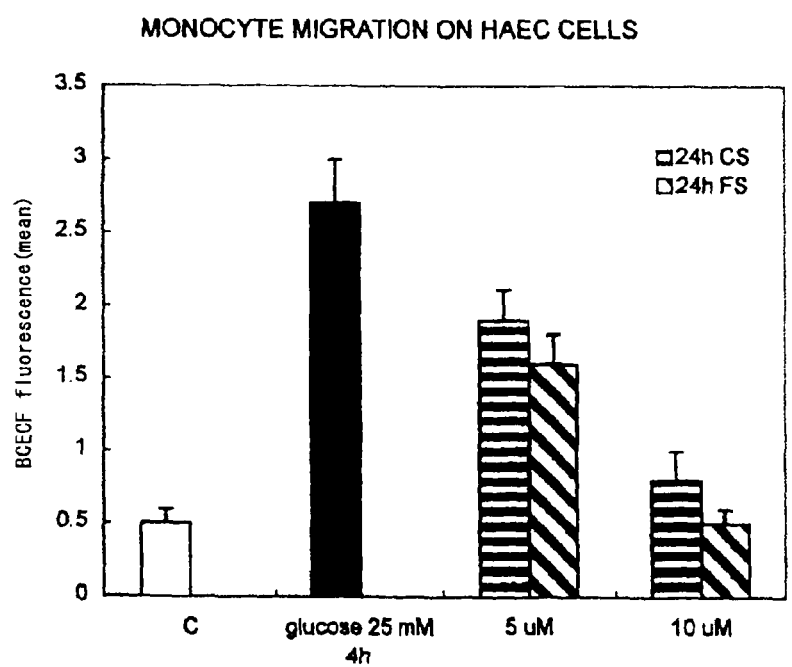
FIG. 8 is a graph showing the investigation results by fluorescence labeling of the effect of a serotonin derivative on the migration capability of monocyte.

As shown in FIG. 7, the number of U-937 cells migrated into subendothelium space increased dramatically by stimulation with high concentration glucose. However, the number of migrated cells significantly decreased by pre-incubation of HAEC cells with CS or FS. Similar results were also confirmed by a fluorescence intensity assay using the fluorescence-labeled U-937 cells (FIG. 8). Therefrom it was shown that a serotonin derivative suppresses migration of monocyte into subendothelium space induced by stimulation with high concentration glucose. From the result of the Example 2 and Example 3, the suppression of migration of monocyte by a serotonin derivative is considered to be attributable to the suppression of MCP-1 production from the endothelial cells.

Example 6

Preparation of Safflower Seed Extract for Animal

A Safflower seed extract was prepared by a method described below. To defatted safflower seed (600 g) after oil extraction was added 3,000 mL of aqueous ethanol (90% by volume) and the mixture was warmed and stirred in a hot-water bath at 60° C. for 3 hours, and then filtered. The same operation was performed once for the solid content after filtration. The obtained filtrates were combined and concentrated under reduced pressure to give 500 mL of a concentrated solution. Water was added to the concentrated solution to 1,000 mL and the content was suspended. The suspension was washed twice with 500 mL of n-hexane and the aqueous layer after washing was extracted twice with 500 mL of ethyl acetate. The ethyl acetate extract was dehydrated with anhydrous magnesium sulfate, filtered and concentrated under reduced pressure to give 10.1 g of a safflower seed extract (SSE). The total serotonin derivative content (aglycone+glycoside) of the extract obtained by this method was 24.1% (21.4% based on aglycone).

Example 7

Action of Ingestion of Serotonin Derivative and Safflower Seed Extract on apoE Knockout Mouse Plasma sVCAM-1 Level 6- to 7-week-old male apoE knockout mice (purchased from Jackson Laboratory) (7-10 mice per group) were divided into the following 5 groups:

1) control,
2) serotonin derivative 0.2% administration group (CS+FS (0.2); CS and FS synthesized in Experimental Example 1, each containing 0.1 wt %),
3) serotonin derivative 0.4% administration group (CS+FS (0.4); CS and FS synthesized in Experimental Example 1, each containing 0.2 wt %),
4) FS 0.4% administration group (FS; containing 0.4 wt % of FS synthesized in Experimental Example 1), and
5) safflower seed extract (SSE) 1% administration group (SSE; containing 1 wt % of SSE obtained in Example 6), and allowed to freely ingest a feed having the composition shown in Table 1 for 15 weeks. After the completion of the dosing period, blood samples were collected from the inferior vena cava (anticoagulant: EDTA-2$K^+$ heparin) of the mice under ether anesthesia, and plasma was collected by centrifugation operation at 3,000 rpm for 15 minutes. The plasma soluble VCAM-1 (sVCAM-1) concentration was measured using a sVCAM-1 measurement ELISA kit "Mouse sVCAM-1/CD106 Quantikine ELISA Kit" (R&D Systems).
The obtained values were subjected to variance analysis among respective groups, and the mean value of the test diet group was compared with that of the control group by Dunnett-test.

Figure 9:
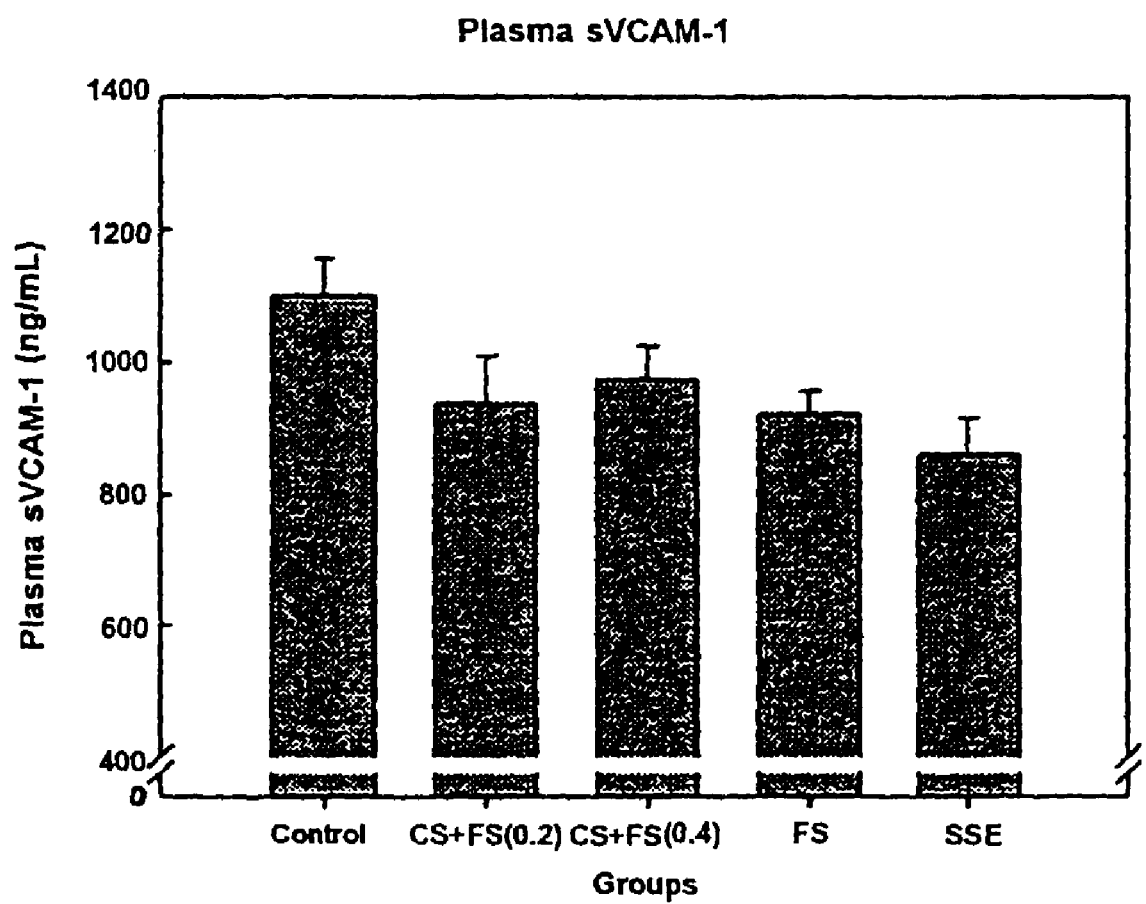
FIG. 9 is a graph showing the investigation results of plasma sVCAM-1 levels in mice which ingested a serotonin derivative.

As shown in FIG. 9, the blood sVCAM-1 level of apoE knockout mice that ingested a serotonin derivative for a long time showed a decreasing tendency in all groups. The animals that ingested SSE showed a statistically significant decrease in the blood sVCAM-1 levels. Therefrom it was confirmed that a serotonin derivative and a safflower seed extract containing a serotonin derivative decrease the VCAM-1 level also in animals.

TABLE 1

| composition | g/Kg feed | | | | |
| --- | --- | --- | --- | --- | --- |
| | Control | CS + FS (0.2) | CS + FS (0.4) | FS | SSE |
| vitamin free casein | 200.0 | 200.0 | 200.0 | 200.0 | 200.0 |
| cornstarch | 632.5 | 630.5 | 628.5 | 628.5 | 622.5 |
| corn oil | 70.0 | 70.0 | 70.0 | 70.0 | 70.0 |
| mineral mixture (AIN-93G) | 35.0 | 35.0 | 35.0 | 35.0 | 35.0 |
| mineral mixture (AIN-93) | 10.0 | 10.0 | 10.0 | 10.0 | 10.0 |
| choline bitartrate | 2.5 | 2.5 | 2.5 | 2.5 | 2.5 |
| cellulose powder | 50.0 | 50.0 | 50.0 | 50.0 | 50.0 |
| CS | | 1.0 | 2.0 | | |
| FS | | 1.0 | 2.0 | 4.0 | |
| SSE | | | | | 10.0 |

Example 8

Preparation of Test Diet for Human Volunteer Test

A safflower seed extract was prepared by a method described below. Defatted safflower seeds (100 kg) were washed with stirring in 2000 L of water at 30° C. for 30 minutes and then subjected to solid-liquid separation. To the obtained solid content was added 1500 L of 60 vol % ethyl alcohol-water. The mixture was heated to 60° C. and stirred at the same temperature for 60 minutes for extraction. Extracts after solid-liquid separation, which were obtained by simultaneously performing the same operation in triplicate, were combined and compression filtrated using a filtration aid (KC floc). An aqueous solution of γ-cyclodextrin (CAVAMAX W8 FOOD, CycloChem. Co. Ltd.) was added in an amount equivalent to that of the solid content of the filtrate, and the mixture was concentrated under reduced pressure at 50 to 60° C. The obtained concentrated solution was heat-sterilized at 88° C. for 1 hour, dried at 60° C. for 15 hours, pulverized and sieved (60 mesh sieve), whereby 6 kg of a safflower seed extract powder was obtained. The analysis results of general components are as shown in Table 2. The total polyphenol content of the safflower seed extract powder was measured by a Folin-Ciocalteau method and found to be 143 mg/g extract powder (p-coumaroyl serotonin equivalent amount). HPLC analysis revealed the total serotonin derivative content of 138 mg/g extract powder (13.8 wt %). The results are shown in Table 3. From the results, a serotonin derivative is considered a major component of phenols contained in the safflower seed extract powder. The safflower seed extract powder thus prepared was filled in a hard capsule by a hard capsule filling machine (Ultra 8, Capsugel Japan Inc.) (210 mg of safflower seed extract powder per one capsule, containing about 29 mg of serotonin derivative).

TABLE 2

Safflower seed extract powder general component composition

| component | content in 100 g of extract |
| --- | --- |
| water | 2.1 g |
| protein | 9.8 g |
| lipid | 3.4 g |
| ash | 3.7 g |
| carbohydrates | 80.2 g |
| dietary fiber | 0.8 g |
| energy | 392 kcal |

TABLE 3

Composition of serotonin derivative in safflower seed extract powder

| component name | content (mg/g extract) |
| --- | --- |
| p-coumaroyl serotonin (CS) | 32.2 |
| ferulyl serotonin (FS) | 31.7 |
| CS monoglucoside | 48.5 |
| FS monoglucoside | 25.7 |
| total serotonin derivative | 138.1 |

Example 9

Action of Ingestion of Safflower Seed Extract Powder on Human Serum sVCAM-1 and MCP-1 Levels 90 male volunteers underwent tests for a second derivative of photoplethysmogram in advance, and 20 therefrom who had a higher second derivative of photoplethysmogram aging index (vascular age) than the chronological age and free of a drug treatment for blood pressure, blood cholesterol or blood glucose control were selected as test subjects (average chronological age 37.3±6.8 years old, average vascular age 48.1±8.1 years old). Ten test diet capsules prepared in Example 8 (safflower seed extract 2.1 g (about 290 mg as serotonin derivative)) were given two times a day (morning and evening, within 30 minutes after meal, 5 each time) every day for 4 weeks, and blood samples were collected (in the morning after over-night fasting) immediately before intake (week 0), at the completion of intake (week 4) and at 4 weeks after the completion of intake (week 8) and the serum was separated. Analysis of serum sVCAM-1 and MCP-1 concentrations was committed to a contract clinical test organization.

During the test diet intake period, no symptoms considered to have been caused by the test diet was reported. Blood biochemical parameters (blood lipid (total cholesterol, HDL-cholesterol, LDL-cholesterol, triglyceride), and blood glucose, liver function indices (GOT, GPT, LDH, γ-GTP total protein, albumin), renal function indices (urea nitrogen, creatinine) and electrocytes ($Na^+$, $K^+$, $Ca^{2+}$)) did not show an abnormal change before and after the intake.

Figure 10:
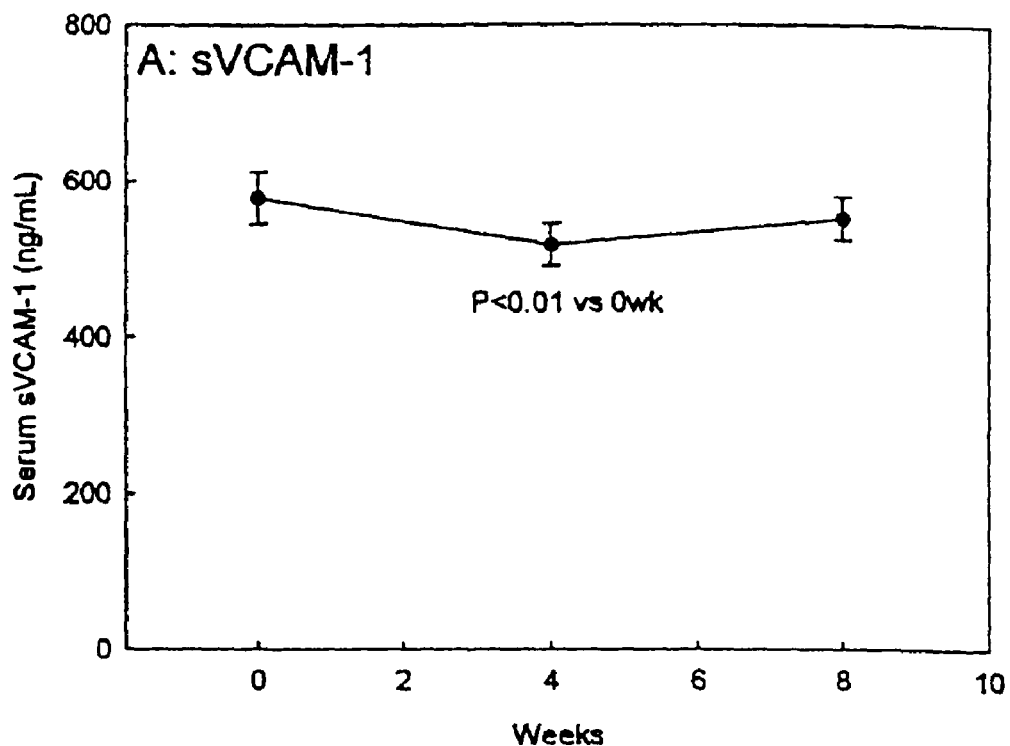
FIG. 10 presents graphs showing the investigation results of serum sVCAM-1(A) and MCP-1(B) levels in human volunteers who ingested a serotonin derivative.
Figure 10:
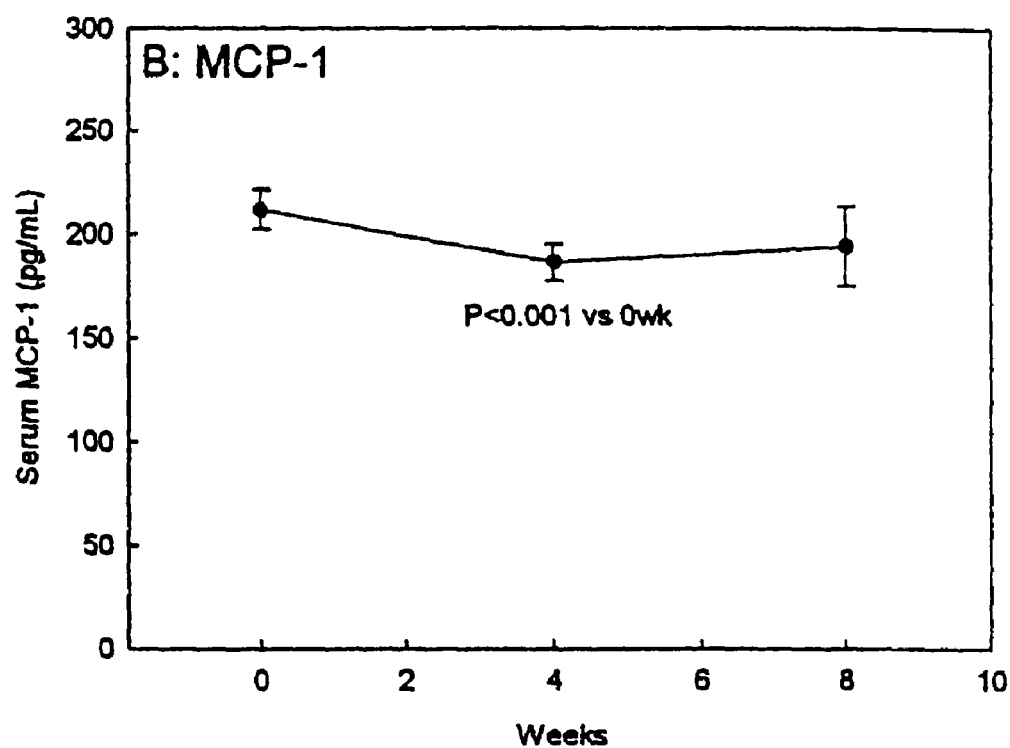

As shown in FIGS. 10A and 10B, by 4 weeks of test diet ingestion, the VCAM-1 and MCP-1 levels in volunteer's serum decreased significantly from those before the start of the test diet ingestion and almost returned to the levels at the start of the test diet ingestion in 4 weeks after the completion of the test diet ingestion. From these results, it was clarified that a safflower seed extract does not have any particular safety problems, and decreases the VCAM-1 and MCP-1 levels also in human.

Example 10

Action of FS-Containing Safflower Seed Extracts (SSE) and FS on Inflammatory Bowel Disease (IBD) Model Mouse Inflammatory bowel disease (IBD) model mice (IL-10 deficient cell-transplanted model) were prepared according to the method of Ikenoue (Ikenoue Y. et al., Int. Immunopharmacol., 5, 993-1006 (2005)) by intraperitoneal administration of a spleen and mesenteric lymph node cell suspension ($1-3 \times 10^7$ cells/200 μL) prepared from IL-10 deficient mouse (7 generation back cross of IL-$10^{-/-}$ mouse confirmed to have developed IBD (diarrhea, body weight decrease) (purchased from Jackson Laboratory) and BALB/c mice (Charles River Laboratory Japan Inc.)) to SCID mice (CB-17/Icr SCID; CLEA Japan, Inc.) (it has already been clarified that, in this animal model, chronic inflammation in the intestine is developed in all cases within 2 to 3 weeks after cell transplantation and the condition can be improved by antiIBD agents (anti-TNF receptor antibody (TNFR-Ig) and steroids (prednisolone)) having a clinically confirmed effect (Ikenoue Y. et al., Int. Immunopharmacol., 5, 993-1006 (2005)).

4 days before IL-10 deficient cell transplantation, total 40 SCID mice (7-week-old, ♀) were divided into the following 4 groups 1) to 4) (10 mice in each group) and acclimation to a control diet was simultaneously started. Immediately after cell transfer, the feed was changed to the test diet shown in Table 4, and free ingestion was allowed for 3 weeks. The safflower seed extract powder was the same as that in Example 8, and contained 50 wt % of γ-cyclodextrin. N-Feruloylserotonin (FS) was synthesized according to the method of Experimental Example 1. During the test diet ingestion period, the body weight, the amount of ingested feed and the amount of water drunk were measured 3 times a week to monitor the onset of the disease.
1) Normal group (normal SCID mice×control diet)
2) Control group (IL-10 deficient cell-transplanted SCID mice×control diet)
3) SSE group (IL-10 deficient cell-transplanted SCID mice×SSE diet*)
4) FS group (IL-10 deficient cell-transplanted SCID mice×FS diet**)
*containing FS and p-coumaroyl serotonin (CS) at 0.10 and 0.13 wt %, respectively (based on aglycone) (total serotonin derivative content=0.28 wt %)
**containing 0.4 wt % of FS aglycone After the completion of the test diet ingestion period, blood samples were collected under anesthesia, and the length of the isolated large intestine (appendix—anus) and the weight thereof (after washing the contents) were measured. Using the obtained data, t-test was first conducted between the Normal group and the Control group and, after confirmation of the effectiveness of the test, variance analyses were performed between the Control group and each of SSE and FS groups, and the effect of the test substance was compared by Dunnett-test.

Figure 11A:
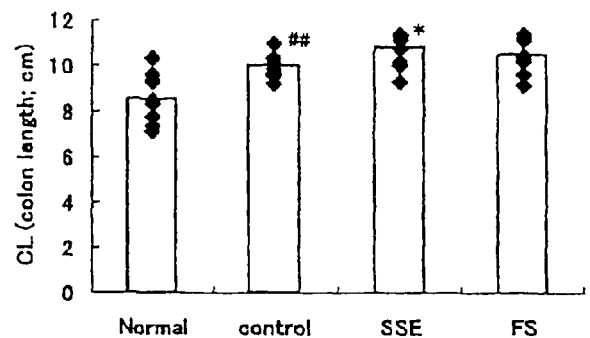
FIG. 11 presents graphs showing the effects of FS and safflower seed extract (SSE) on the length of large intestine (A), large intestine weight (B) and large intestine weight per unit length (C) of IBD model mice (IL-10 deficient cell-transplanted SCID mice).
Figure 11B:
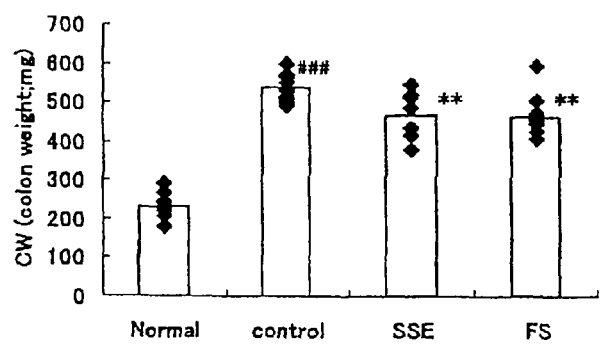
Figure 11C:
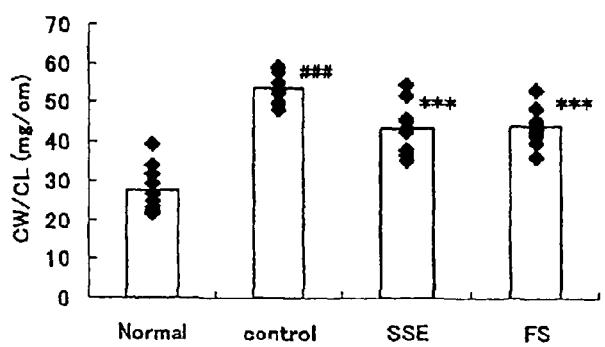
Figure 12C:
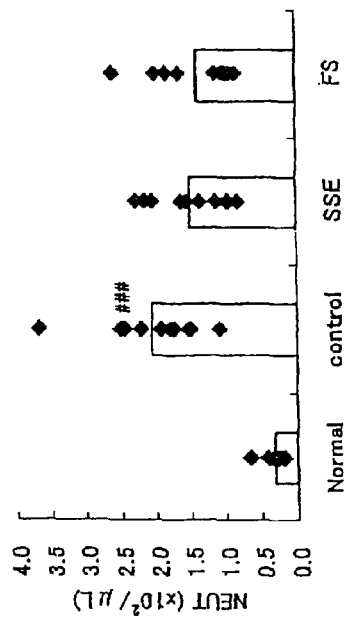
FIG. 12 presents graphs showing the effects of FS and safflower seed extract (SSE) on leukocyte count (A), platelet count (B), neutrophil count (C) and monocyte count (D) of IBD model mice (IL-10 deficient cell-transplanted SCID mice).
Figure 12D:
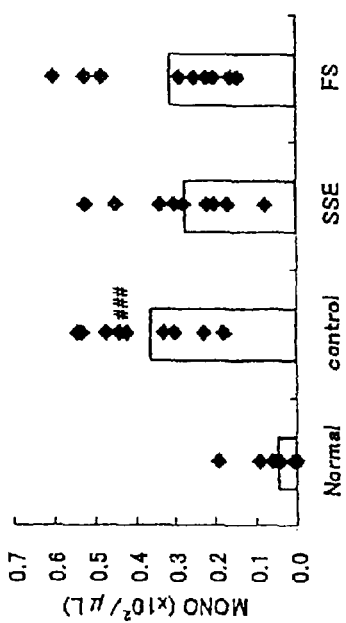
Figure 12A:
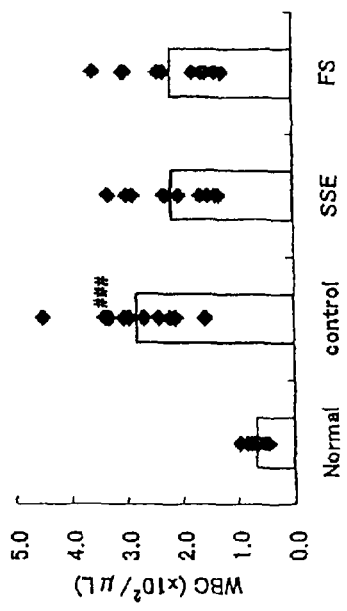
Figure 12B:
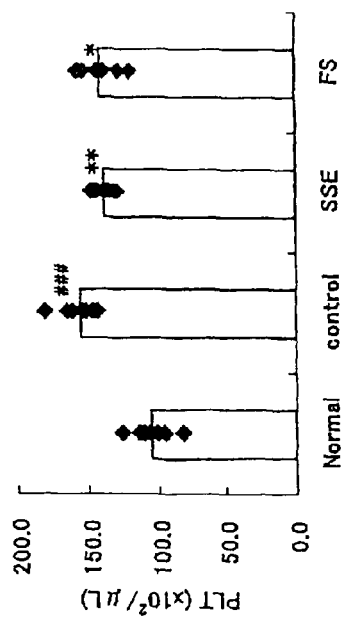

As shown in Table 5, IL-10 deficient cell transfer significantly suppressed body weight gain. As for the amount of ingested feed and the amount of water intake, a significant difference was not found between groups. In contrast, as shown in FIG. 11, the control group showed a significant increase in the large intestine length, large intestine weight, and large intestine weight per unit intestine length due to the IL-10 deficient cell transplantation. As shown in FIG. 12, moreover, since the blood leukocyte count, platelet count, neutrophil count and monocyte count significantly increased, the development of colitis was obvious. The animal that ingested SSE and FS showed significantly lower values of large intestine weight and large intestine weight per unit intestine length than those of the control group. In addition, in all groups, the platelet count was significantly lower than that of the Control group (the above-mentioned document (Ikenoue Y. et al., Int. Immunopharmacol., 5, 993-1006 (2005)) teaches that the platelet count increases with pathological progression in this model). Although the leukocyte count, neutrophil count and monocyte count were not statistically significant, the SSE group and FS group showed tendency toward lower values in all of them than the Control group. These results reveal that the ingestion of SSE and FS improves colitis.

TABLE 4

| | g/Kg feed | | |
|---|---|---|---|
| feed composition | control diet | SSE diet | FS diet |
| vitamin free casein | 200.0 | 200.0 | 200.0 |
| cornstarch | 632.5 | 612.5 | 618.5 |
| corn oil | 70.0 | 70.0 | 70.0 |
| mineral mixture (AIN-93G) | 35.0 | 35.0 | 35.0 |
| mineral mixture (AIN-93) | 10.0 | 10.0 | 10.0 |
| choline bitartrate | 2.5 | 2.5 | 2.5 |
| cellulose powder | 50.0 | 50.0 | 50.0 |
| FS | — | — | 4.0 |
| safflower seed extract powder | — | 20.0 | — |
| γ-cyclodextrin | 10.0 | — | 10.0 |

TABLE 5

Body weight, amount of ingested feed, amount of water drunk.

| | body weight (g) mean ± SEM | | | |
|---|---|---|---|---|
| group | start of test diet ingestion (day 0) | completion of test diet ingestion (day 21) | change rate (day 0 = 100) | significant difference (vs Control) |
| Normal | 18.9 ± 0.4 | 21.7 ± 0.4 | 114.9 ± 1.6 | P = 0.026 |
| Control | 18.6 ± 0.3 | 20.2 ± 0.4 | 109.1 ± 1.8 | |
| SSE | 18.9 ± 0.5 | 20.6 ± 0.3 | 109.9 ± 2.2 | NS |
| FS | 18.3 ± 0.3 | 20.6 ± 0.4 | 112.5 ± 1.2 | NS |

TABLE 5-continued

Body weight, amount of ingested feed, amount of water drunk.

amount of ingested feed, amount of water drunk (g/day/mouse) mean ± SEM

| group | average amount of ingested feed during test period | significant difference (vs Control) | average amount of water drunk during test period | significant difference (vs Control) |
|---|---|---|---|---|
| Normal | 3.3 ± 0.1 | NS | 2.3 ± 0.2 | NS |
| Control | 3.3 ± 0.1 | | 2.3 ± 0.2 | |
| SSE | 3.0 ± 0.1 | NS | 2.3 ± 0.2 | NS |
| FS | 3.2 ± 0.1 | NS | 2.2 ± 0.2 | NS |

Figure 13:
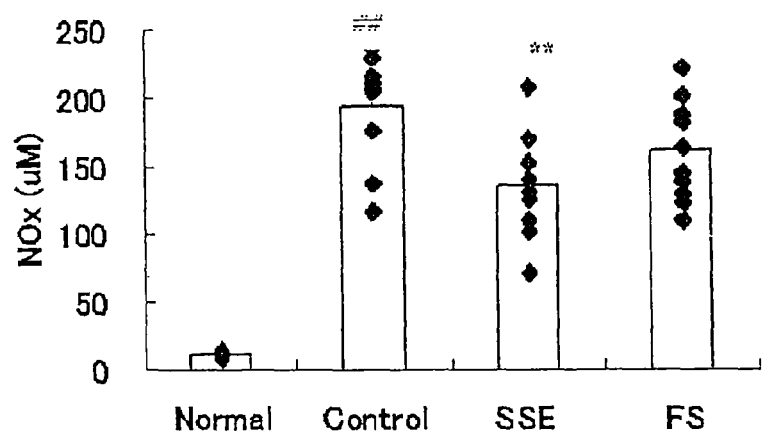
FIG. 13 is a graph showing the effects of FS and safflower seed extract (SSE) on the blood NOx concentration of IBD model mice (IL-10 deficient cell-transplanted SCID mice).

By the activation of leukocytes in an inflammatory response, a large amount of NO is produced by the cells, and the blood concentration of NOx, a metabolite, increases. It is known that blood NOx concentration becomes one index of inflammatory response in living organisms due to this mechanism (Yuka Ikenoue et al., International Immunopharmacology 5 (2005) 993-1006). The NOx concentration of the blood obtained in Example 10 was measured using an "Nitric Oxide Quantitation Kit (ACTIVE MOTIF)". As a result, as shown in FIG. 13, the Control group showed a marked increase in the NOx concentration as compared to the Normal group. In contrast, the SSE group showed a significant decrease in the NOx concentration, and the FS group showed tendency toward decrease, although a statistically significant difference was not found.

At the end of the test described in Example 10, the large intestine (caecum—anus) was cut into about 1 cm pieces from the center to the anus side to give 3 sections in total. One of them was fixed with 10% formalin solution and two were frozen in liquid nitrogen. The large intestine fixed with formalin was embedded in paraffin, and sliced to give transversely sectioned specimens. The specimens were stained by a PAS (Periodic acid Schiff) staining method, and histopathological images were observed. On the other hand, total RNA was extracted from the frozen large intestine tissue with ISOGEN (NIPPON GENE CO., LTD.) Total RNA (2 µg) was subjected to a reverse transcription reaction using a SYBR ExScript™ RT-PCR kit (TaKaRa) and, using this as a template, quantitative realtime PCR was performed using IL-1β, TNF-α and GAPDH. The primers used for the analysis were as follows.

```
IL-1β: forward 5'- TCA CAG CAG CAC ATC AAC AA -3' (SEQ ID NO: 7)
       reverse 5'- TGT CCT CAT CCT GGA AGG TC -3' (SEQ ID NO: 8)

TNF-α: forward 5'- CCA CCA CGC TCT TCT GTC TA -3' (SEQ ID NO: 9)
       reverse 5'- AGG GTC TGG GCC ATA GAA CT -3' (SEQ ID NO: 10)

GAPDH: forward 5'- CTG AGG ACC AGG TTG TCT CC -3' (SEQ ID NO: 11)
       reverse 5'- ACC ACC CTG TTG CTG TAG CC -3' (SEQ ID NO: 12)
```

Template DNA (2 µl), SYBR Premix Ex Taq™ (TaKaRa, 10 µl), ROX Reference Dye (0.4 µl), 100 µM forward primer (0.04 µl), 100 µM reverse primer (0.04 µl) and sterile water (7.52 µl) were mixed on ice and, using Applied Biosystems 7900HT Fast realtime PCR system, the mixture was heated at 95° C. for 10 seconds, followed by 40 cycles of 95° C., 5 seconds and 60° C., 34 seconds, whereby the DNA was amplified. Using GAPDH as the internal standard, IL-1β and TNF-α expression levels were evaluated.

Figure 14:
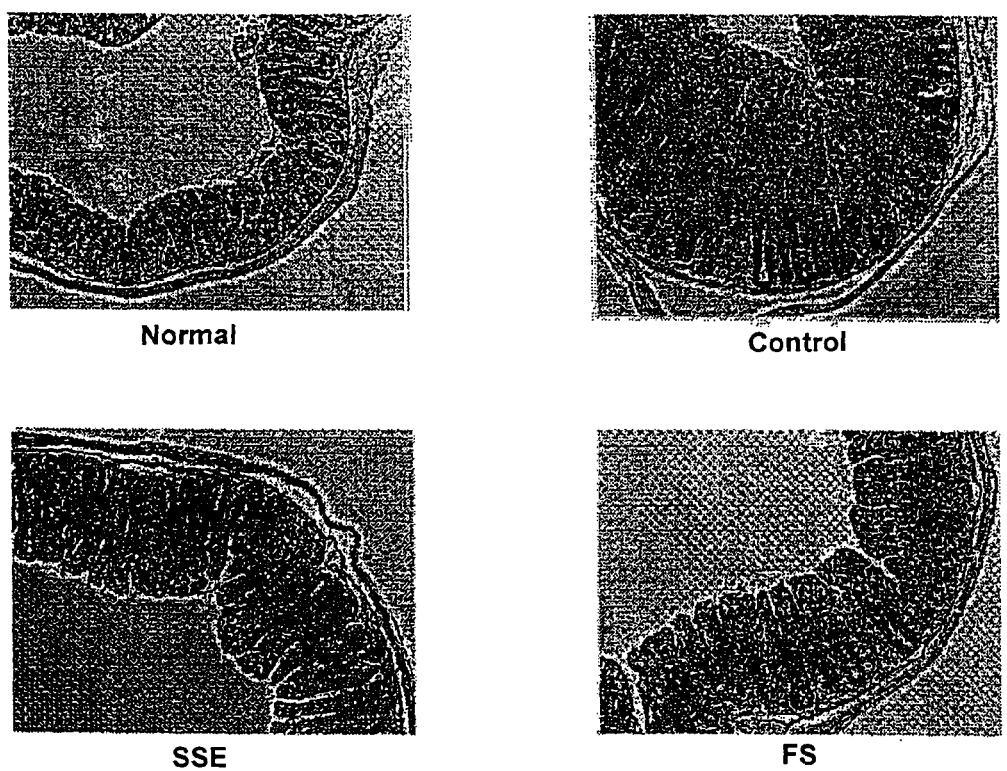
FIG. 14 presents photographs showing the effects of FS and safflower seed extract (SSE) on a large intestine pathological tissue of IBD model mice (IL-10 deficient cell-transplanted SCID mice).
Figure 15:
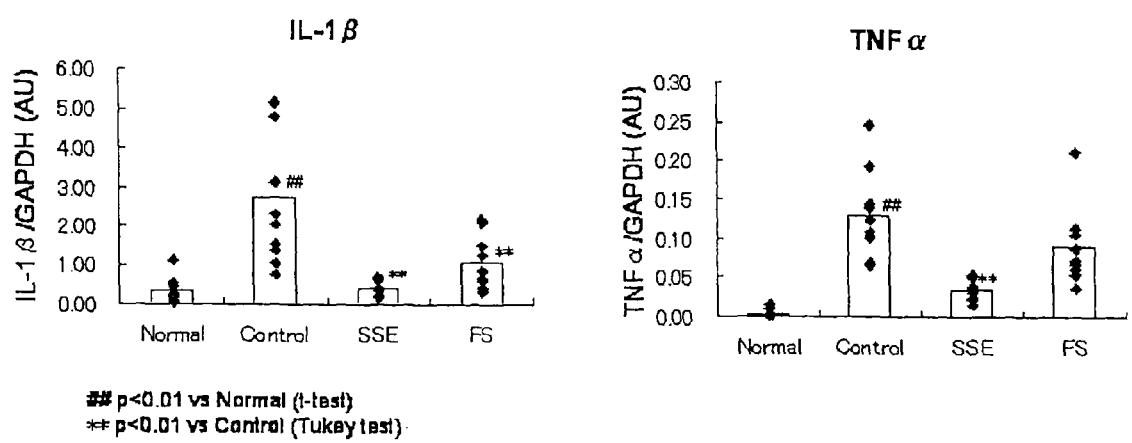
FIG. 15 is a graph showing the effects of FS and safflower seed extract (SSE) on the gene expression of IL-1β and TNF-α in a large intestine tissue of IBD model mice (IL-10 deficient cell-transplanted SCID mice).

As shown in FIG. 14, the Control group showed pathological observations characteristic of inflammatory bowel disease, such as remarkable thickening of large intestine mucosal epithelium and decreased normal size goblet cell count (Yuka Ikenoue et al., International Immunopharmacology 5 (2005) 993-1006). In comparison with the Control group, the SSE group and FS group showed observations of suppressed thickening of the large intestine mucosal epithelium and increased number of normal goblet cells, thus demonstrating improvement effects by pathological observations. Furthermore, as regards the mRNA expression levels of IL-1β and TNF-α, which are inflammatory cytokines, in large intestine tissues, both the SSE group and FS group showed a significant decrease in IL-1β as compared to the Control group and the SSE group showed a significant decrease and the FS group showed tendency toward decrease in TNF-α (FIG. 15).

The effects in the SSE group and FS group on the blood NOx level, histopathological observations and the mRNA expression levels of inflammatory cytokines strongly suggest that the effects of decreased large intestine weight and decreased large intestine weight per unit intestine length are attributable to the suppression of inflammatory response in the large intestine.

INDUSTRIAL APPLICABILITY

The product of the present invention enables wide prevention or treatment of inflammatory diseases via an NF-κB activation suppressive action. Specifically, the disease includes chronic arthritis, psoriasis, inflammatory bowel disease, endometriosis and the like, and particularly, improvement or prophylaxis of inflammatory bowel disease is expected. In addition, the product of the present invention enables prevention or treatment of diseases relating to NF-κB activation. Specific examples include diseases such as the aforementioned inflammatory disease, virus infection, metastasis of tumor, immune disease and the like. Moreover, the product of the present invention enables prevention or treatment of diseases caused by expression of VCAM-1 and/or MCP-1 via NF-κB. Specific examples include diseases such as intractable inflammatory immune diseases (e.g., pulmonary hypertension, rheumatoid arthritis, hepatofibrosis and the like), atherosclerosis after organ transplantation and the like. In addition to use as a pharmaceutical product, the product of the present invention can also be applied to food.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method for treating inflammatory bowel disease in a subject in need thereof, comprising administering feruloyl serotonin to said subject in need thereof in an amount of from 20 mg to 2 g per day.

2. The method of claim 1, wherein the feruloyl serotonin is contained in a pharmaceutical composition.

3. The method of claim 1, wherein the feruloyl serotonin is contained in a food.

4. The method of claim 3, wherein the food is a dietary supplement.

5. The method of claim 1, wherein the feruloyl serotonin is administered to said subject in need thereof in a single dosage.

6. The method of claim 1, wherein the feruloyl serotonin is administered to said subject in need thereof in several portions a day.

7. The method of claim 1, wherein the feruloyl serotonin is administered to said subject in need thereof as a safflower seed extract.

8. The method of claim 7, wherein the feruloyl serotonin is administered orally.

9. The method of claim 1, wherein said feruloyl serotonin is administered in an amount sufficient to maintain a blood concentration thereof of 0.1 to 10,000 nM.

10. The method of claim 1, wherein said feruloyl serotonin is administered in an amount sufficient to maintain a blood concentration thereof of 1-5,000 nM.

11. The method of claim 1, wherein said feruloyl serotonin is administered in an amount sufficient to maintain a blood concentration thereof of 100-1,000 nM.

* * * * *

SEQUENCE LISTING

<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cccttgaccg gctggagatt                                              20

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctgggggcaa cattgacata aagtg                                        25

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cgcctccagc atgaaagtct                                              20

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggaatgaagg tggctgctat g                                            21

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
accacagtcc atgccatcac                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer -continued

```
<400> SEQUENCE: 6
tccaccaccc tgttgctgta                                           20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tcacagcagc acatcaacaa                                           20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tgtcctcatc ctggaaggtc                                           20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ccaccacgct cttctgtcta                                           20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
agggtctggg ccatagaact                                           20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ctgaggacca ggttgtctcc                                           20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 12
accaccctgt tgctgtagcc                                              20
```